(12) United States Patent
Beane et al.

(10) Patent No.: US 8,277,465 B2
(45) Date of Patent: Oct. 2, 2012

(54) APPARATUS AND METHOD FOR CONNECTING A CONDUIT TO A HOLLOW VESSEL

(75) Inventors: Richard M. Beane, Hingham, MA (US); John W. Brown, Indianapolis, IN (US); James Alan Crunkleton, Weston, MA (US); James S. Gammie, Stevenson, MD (US); Joseph L. Smith, Jr., Concord, MA (US)

(73) Assignee: Correx, Inc., Waltham, MA (US)

( * ) Notice: Subject to any disclaimer, the term of this patent is extended or adjusted under 35 U.S.C. 154(b) by 1133 days.

(21) Appl. No.: 11/300,589

(22) Filed: Dec. 15, 2005

(65) Prior Publication Data
US 2006/0161193 A1 Jul. 20, 2006

Related U.S. Application Data

(63) Continuation-in-part of application No. 11/086,577, filed on Mar. 23, 2005, now Pat. No. 7,510,561.

(60) Provisional application No. 60/636,449, filed on Dec. 15, 2004, provisional application No. 60/726,223, filed on Oct. 14, 2005, provisional application No. 60/726,222, filed on Oct. 14, 2005.

(51) Int. Cl.
*A61B 17/11* (2006.01)

(52) U.S. Cl. .......................................................... 606/153

(58) Field of Classification Search .................. 606/153, 606/184, 191, 192, 194, 198; 623/1.11, 1.13, 623/1.23, 1.35
See application file for complete search history.

(56) References Cited

U.S. PATENT DOCUMENTS 4,118,806 A 10/1978 Porier
(Continued)

FOREIGN PATENT DOCUMENTS

WO WO 82/01644 A 5/1982
(Continued)

OTHER PUBLICATIONS

Berger et al., Replacement of the Thoracic Aorta With Intraluminal Sutureless Prosthesis, The Annals of Thoracic Surgery, 1992, 920-927, vol. 53.
(Continued)

*Primary Examiner* — Ryan Severson
(74) *Attorney, Agent, or Firm* — Pandiscio & Pandiscio

(57) ABSTRACT

The present invention provides a system and method for forming a side branch on a hollow vessel, such as the aorta. The side branch is preferably adapted to be connected to a connector conduit, but any other suitable use is also acceptable. The system comprises a graft including a side branch portion, and an applicator comprising a hole forming element adapted to form a hole in the wall of the vessel and an insertion element adapted to be inserted through the wall of the vessel, the insertion element comprising a retraction element adapted to enter into engagement with the graft. The hole forming element may comprise a cutting element adapted to cut a hole in the wall of the vessel, and a positioning element adapted to hold the position of the applicator relative to the vessel. The system further comprises a graft protection element adapted to prevent the graft from being damaged by the cutting element. In this case, the clamping element and the graft protection element may be the same element, for example, an expansion element, which may be expandable from an unexpanded state to fully expanded state and to a partially expanded state. The expansion element may be a balloon, which may be in the shape of a circular toroid, and may include a tension member that restricts the dimensions of the balloon. In addition, the expansion element may be an umbrella mechanism.

33 Claims, 14 Drawing Sheets

U.S. PATENT DOCUMENTS

| | | | |
|---|---|---|---|
| 4,769,031 A | 9/1988 | McGough | |
| 4,794,928 A | 1/1989 | Kletschka | |
| 5,129,913 A | 7/1992 | Ruppert | |
| 5,500,014 A | 3/1996 | Quijano | |
| 5,843,088 A | 12/1998 | Barra | |
| 6,083,237 A | 7/2000 | Huitema | |
| 6,146,325 A | 11/2000 | Lewis | |
| 6,266,550 B1 | 7/2001 | Selmon | |
| 6,395,015 B1 * | 5/2002 | Borst et al. | 606/213 |
| 6,409,739 B1 | 6/2002 | Nobles | |
| 6,416,527 B1 | 7/2002 | Berg | |
| 6,475,222 B1 | 11/2002 | Berg | |
| 6,551,350 B1 | 4/2003 | Thornton et al. | |
| 6,626,921 B2 * | 9/2003 | Blatter et al. | 606/153 |
| 6,712,831 B1 | 3/2004 | Kaplan | |
| 6,726,648 B2 | 4/2004 | Kaplon | |
| 6,732,501 B2 | 5/2004 | Yu et al. | |
| 6,802,806 B2 | 10/2004 | McCarthy et al. | |
| 6,814,747 B2 * | 11/2004 | Anson et al. | 623/1.13 |
| 6,827,735 B2 | 12/2004 | Greenberg | |
| 6,843,803 B2 | 1/2005 | Ryan et al. | |
| 6,863,677 B2 | 3/2005 | Breznock | |
| 6,893,460 B2 | 5/2005 | Spenser et al. | |
| 6,942,672 B2 | 9/2005 | Heilman | |
| 6,994,666 B2 | 2/2006 | Shannon | |
| 7,048,681 B2 | 5/2006 | Tsubouchi et al. | |
| 7,077,801 B2 | 7/2006 | Haverich | |
| 7,172,550 B2 | 2/2007 | Tsubouchi | |
| 7,510,561 B2 | 3/2009 | Beane et al. | |
| 2001/0004675 A1 | 6/2001 | Woodard | |
| 2001/0004697 A1 | 6/2001 | Blatter et al. | |
| 2001/0005787 A1 | 6/2001 | Oz et al. | |
| 2001/0025643 A1 | 10/2001 | Foley | |
| 2002/0045846 A1 | 4/2002 | Kaplon | |
| 2002/0082467 A1 | 6/2002 | Campbell | |
| 2002/0082614 A1 | 6/2002 | Logan | |
| 2002/0173808 A1 | 11/2002 | Houser | |
| 2002/0183584 A1 | 12/2002 | Shannon et al. | |
| 2002/0183769 A1 | 12/2002 | Swanson et al. | |
| 2003/0023255 A1 | 1/2003 | Miles | |
| 2003/0033008 A1 * | 2/2003 | Schmitt et al. | 623/1.51 |
| 2003/0040765 A1 | 2/2003 | Breznock | |
| 2003/0078592 A1 | 4/2003 | Heilman et al. | |
| 2003/0100816 A1 | 5/2003 | Siess | |
| 2003/0130668 A1 | 7/2003 | Nieman | |
| 2004/0002624 A1 | 1/2004 | Yu et al. | |
| 2004/0002719 A1 | 1/2004 | Oz et al. | |
| 2004/0059178 A1 | 3/2004 | McCarthy et al. | |
| 2004/0116769 A1 | 6/2004 | Jassawalla et al. | |
| 2004/0162608 A1 | 8/2004 | Haverich | |
| 2004/0171905 A1 | 9/2004 | Yu et al. | |
| 2004/0193004 A1 | 9/2004 | Tsubouchi et al. | |
| 2004/0215220 A1 * | 10/2004 | Dolan et al. | 606/153 |
| 2005/0033107 A1 | 2/2005 | Tsubouchi | |
| 2005/0149093 A1 | 7/2005 | Pokorney | |
| 2006/0036313 A1 | 2/2006 | Vassiliades | |
| 2006/0089707 A1 | 4/2006 | Vassiliades | |
| 2006/0241544 A1 | 10/2006 | Haverich | |
| 2007/0055357 A1 | 3/2007 | Pokorney et al. | |

FOREIGN PATENT DOCUMENTS

| | | |
|---|---|---|
| WO | WO 93/00868 A | 1/1993 |
| WO | WO 97/27897 | 8/1997 |
| WO | WO 2004/073555 | 9/2004 |

OTHER PUBLICATIONS

Brown, J.W. et al., Apicoaortic Valved Conduits for Complex Left Ventricular Outflow Obstruction: Technical Considerations and Current Status, The Annals of Thoracic Surgery, Aug. 1984, pp. 162-168, vol. 38(2).

Carrel, A., On the Experimental Surgery of the Thoracic Aorta and the Heart, May 5, 1910, pp. 83-95.

Sarnoff, S.J. et al., The Surgical Relief of Aortic Stenosis by Means of Apical-Aortic Valvular Anastomosis, Circulation, 1955, pp. 564-575, vol. 11.

* cited by examiner

APPARATUS AND METHOD FOR CONNECTING A CONDUIT TO A HOLLOW VESSEL

RELATED APPLICATION DATA

This application is a continuation-in-part of U.S. patent application Ser. No. 11/086,577 filed Mar. 23, 2005, and claims priority to U.S. Provisional Patent Application Nos. 60/636,449 filed on Dec. 15, 2004, 60/726,223 filed Oct. 14, 2005, and 60/726,222 filed Oct. 14, 2005, the disclosures of which are hereby incorporated by reference in their entirety.

FIELD OF THE INVENTION

The present invention relates to an apparatus and method for connecting a conduit to a hollow vessel, and more particularly, to a surgical device connectable to the aorta to bypass the aortic valve.

BACKGROUND

As the average age of the United States population increases, so do the instances of aortic stenosis. An alternative approach to the conventional surgical replacement of the stenotic aortic valve involves the use of an apicoaortic conduit. In this approach, the native aortic valve is not removed, and a prosthetic valve is implanted in a parallel flow arrangement. A connection conduit (or tube) connects the apex of the heart to the descending aorta. Somewhere along this conduit, the prosthetic valve is interposed. Thus, blood leaves the heart through the apex and travels through the conduit (with valve) to the descending aorta.

Until recently, surgical procedures to implant an apicoaortic conduit have included a single, long incision, such as in the $6^{th}$ intercostal space, to expose the heart and allow retraction of the lungs to expose the descending aorta. Recognizing the potential for broader scale use of the apicoaortic conduit for aortic valve replacement, some surgeons are now attempting to use smaller incisions and are requesting development of surgical tools for a minimally invasive procedure. As an initial attempt to make the procedure less invasive, some surgeons have recently performed the following procedure.

The patient is placed on the table in the supine position. Anesthesia is induced, and the patient is intubated with a double-lumen endotracheal tube, this facilitates one-lung ventilation and allows the surgeon to work within the left chest. The patient is positioned with the left side up (90 degrees). The pelvis is rotated about 45 degrees, such that the femoral vessels are accessible. An incision is made over the femoral vessels, and the common femoral artery and vein are dissected out. Heparin is administered. Pursestring sutures are placed in the femoral artery and vein. The artery is cannulated first, needle is inserted into the artery, and a guidewire is then inserted. Transesophageal echo is used to ascertain that the wire is in the descending aorta. Once this is confirmed, a Biomedicus arterial cannula is inserted over the wire, into the artery (Seldinger technique). The arterial cannula is typically 19 or 21 French. Once inserted, the pursestring sutures are snugged down over tourniquets. A similar procedure is followed for the femoral vein. The venous cannula is usually a few French larger than the arterial cannula. Once both vein and artery are cannulated, the cannulae are connected to the cardiopulmonary bypass, and the capability to initiate cardiopulmonary bypass at any time is present.

A 1 cm incision is made in approximately the $7^{th}$ interspace in the posterior auxiliary line; the videoscope (10 mm diameter) is inserted, and the left chest contents viewed. The location of the apex of the heart is determined, and the light from the scope used to transilluminate the chest wall; this allows precise localization of the incision. The incision is then performed; it is essentially an anterior thoracotomy, typically in the $6^{th}$ interspace. Recent incisions have been about 10 cm long, but are expected to become smaller and smaller with time. A retractor is inserted and the wound opened gently. A lung retractor is used to move the (deflated) left lung cephalad. The descending aorta is dissected free from surrounding soft tissue to prepare for the distal anastomosis. This dissection includes division of the inferior pulmonary ligament. A pledgeted suture is placed on the dome of the diaphragm and positioned to pull the diaphragm toward the feet (out of the way). The pericardium is incised about the apex of the heart, and the apex is freed up and clearly identified.

On the back table, the apicoaortic conduit is prepared: a 21 freestyle valve is sutured to an 18 mm Medtronic apical connector. The valve is also sutured to a 20 mm Hemashield graft. The Dacron associated with the apical connector is pre-clotted with thrombin and cryoprecipitate. The assembly is brought to the field, and a measurement made from the apex of the heart to the descending aorta. The assembly is trimmed appropriately. A partial-occluding clamp is then placed on the descending aorta, and the aorta opened with a knife and scissors. The conduit (the end with the 20 mm hemashield graft) is then sutured to the descending aorta using 4-0 prolene suture, in a running fashion. Once this is complete, the clamp is removed and the anastomosis checked for hemostasis. Blood is contained by the presence of the freestyle aortic valve. The apical connector is placed on the apex, and a marker is used to trace the circular outline of the connector on the apex, in the planned location of insertion. Four large pledgeted sutures (mattress sutures) of 2-0 prolene are placed; one in each quadrant surrounding the marked circle. The sutures are then brought through the sewing ring of the apical connector. A stab wound is made in the apex in the center of the circle, and a tonsil clamp is used to poke a hole into the ventricle. To date, bypass has been initiated at this point, but doing so may not be necessary. A Foley catheter is inserted into the ventricle, and the balloon expanded. A cork borer is then used to cut out a plug from the apex. The connector is then parachuted down into position. A rotary motion is necessary to get the connector to seat in the hole. The four quadrant sutures are tied, and hemostasis is checked. If there is a concern regarding hemostasis, additional sutures are placed. The retractor is removed, chest tubes are placed, and the wound is closed.

Surgical tools developed specifically to implant the apicoaortic conduit are expected to provide the means for a much less invasive procedure. The procedure is expected to be performed with a series of smaller thoracotomy incisions between the ribs, such as immediately over the apex of the heart. In addition to avoiding the median sternotomy, development of appropriate surgical tools is expected to avoid the need for cardiopulmonary bypass, so that the procedure can be performed on a beating heart. The diseased aortic valve does not need to be exposed or excised. The stenotic aortic valve is left in place and continues to function at whatever level it remains capable of, and the apicoaortic conduit accommodates the balance of aortic output.

The major obstacle to widespread adoption of this superior technique is the nearly complete lack of efficient devices to perform the procedure. Surgeons wishing to adapt the procedure must gather a collection of instruments from a variety of manufacturers. Often these instruments were created for quite different purposes, and the surgeon is forced to adapt them as required and manually manipulate them during a procedure.

A less invasive means to implant the apical connector is described in U.S. patent application Ser. No. 11/086,577, which is hereby incorporated by reference in its entirety. A customized apical connector with an insertion tool referred to as an applicator is described therein. Also described is a quick connect coupler, which may be employed by the invention described herein. The apical connector invention allows the apical connector to be implanted without use of cardiopulmonary bypass and with a negligible amount of blood loss. Although this prior invention provides a key enabling technology that will allow mainstream use of the apicoaortic procedure, additional surgical tools and prostheses are needed to make the procedure even less invasive.

SUMMARY OF THE INVENTION

An object of the present invention is to provide the necessary surgical tools and prostheses to enable combined percutaneous and minimally invasive surgical techniques to implant the aortic connector of the apicoaortic conduit with minimal blood loss.

Another object of the present invention is to allow the surgeon to precisely select the site for anastomosis by inserting the distal end of an applicator into the aorta at the selected site.

Another object of the present invention is to provide an applicator that includes a cutter that cuts a hole in the aorta with negligible blood loss. Embodiments of the applicator may use a balloon or a cutter guard to protect the prosthesis from the cutter.

Another object of the present invention is to mechanically coordinate movement of some of the components of the applicator to provide safety and ease of use for the surgeon.

Another object of the present invention is to provide an aortic connector that establishes an anastomosis between the descending aorta and the portion of the apicoaortic conduit prosthesis not included in the aortic connector. The aortic connector includes an aortic graft that is deployed within the aorta and a side branch that will extend through the aorta wall at the site selected by the surgeon. The side branch is folded inside the aortic graft until after the aortic branch is expanded. The side branch may include a quick connect coupler and an occlusion means. The occlusion means may be a sewn seam or a prosthetic valve, as examples.

Thus, the present invention provides an applicator for forming a hole in a wall of a hollow vessel, such as the aorta, and engaging a graft. The applicator comprises a hole forming element adapted to form a hole in the wall of the vessel and an insertion element adapted to be inserted through the wall of the vessel. The hole forming element comprises a cutting element adapted to cut a hole in the wall of the vessel and a positioning element adapted to hold the position of the applicator relative to the vessel, and the insertion element comprises a retraction element adapted to enter into engagement with a graft. The applicator may further comprise a graft protection element adapted to prevent the graft from being damaged by the cutting element.

The positioning element may further comprise a reaction element adapted to be positioned on the outside of the wall of the vessel, and a clamping element adapted to be positioned on the inside of the wall of the vessel, wherein the wall of the vessel may be held between the reaction element and the clamping element, thereby holding the position of the applicator relative to the vessel. In addition, the cutting element may be a cutting blade, and may be cylindrically shaped.

The clamping element may be formed of any suitable material. For example, the clamping element may be an expansion element, such as a balloon, or may be made of a rigid material, such as a clamp pad. In addition, it is preferred that the clamping element be adapted to prevent a tissue plug from entering the vessel, the tissue plug comprising the portion of the wall removed when the hole is formed in the vessel.

The retraction element may comprise a graft attachment tool, which is preferably radiopaque. In addition, the retraction element may be further adapted to be withdrawn from the hole formed in the wall of the vessel after entering into engagement with the graft, thereby withdrawing a portion of the graft. In this case, the portion of the graft withdrawn by the retraction element forms a side branch to the vessel. The insertion element may also comprise a trocar.

The present invention also provides a method for forming a hole in a wall of a hollow vessel, such as the aorta, and engaging a graft. The method comprises inserting an insertion element through the wall of the vessel until at least a portion of a retraction element of the insertion element may be positioned within the vessel, positioning the wall of the vessel relative to the applicator with a positioning element, engaging the graft with the retraction element, and forming the hole in the wall of the vessel with the cutting element.

The cutting element may be a cutting blade, and the forming step may comprise pressing the cutting blade into the wall of the vessel and applying torsional force to the cutting blade. Also, the insertion element may further comprise a trocar.

The positioning step may comprise biasing, or positioning, a reaction element on the outside of the wall of the vessel, biasing, or positioning, a clamping element on the inside of the wall of the vessel, and holding the wall of the vessel between the reaction element and the clamping element. The clamping element may be a balloon, or may be made of a rigid material, such as a clamp pad. In addition, the clamping element may be adapted to prevent a tissue plug from entering the vessel, the tissue plug comprising the portion of the wall removed when the hole may be formed in the vessel.

The method may also comprise positioning a graft protection element between the graft and the cutting element prior to the forming step, and the graft may be predisposed within the vessel. Also, the retraction element may comprise a graft attachment tool, which is preferably radiopaque. The method may further comprise of withdrawing the retraction element from the hole formed in the wall of the vessel after the steps of engaging and forming, thereby withdrawing a portion of the graft, which preferably forms a side branch to the vessel.

The present invention also provides a system for forming a side branch on a hollow vessel, such as the aorta. The side branch is preferably adapted to be connected to a connector conduit, such as the remainder of an apical aortic prothesis, but any other suitable use is also acceptable. The system further comprises a graft including a main vessel portion and a side branch portion, and an applicator comprising a hole forming element adapted to form a hole in the wall of the vessel and an insertion element adapted to be inserted through the wall of the vessel, the insertion element comprising a retraction element adapted to enter into engagement with the graft. The side branch portion of the graft is preferably maintained in a compressed state prior to the formation of the side branch. In addition, the insertion element may include a trocar.

The hole forming element may comprise a cutting element adapted to cut a hole in the wall of the vessel, and a positioning element adapted to hold the position of the applicator relative to the vessel. The positioning element comprises a reaction element adapted to be positioned on the outside of the wall of the vessel, and a clamping element adapted to be positioned on the inside of the wall of the vessel, wherein the wall of the vessel may be held between the reaction element and the clamping element, thereby holding the position of the applicator relative to the vessel. The cutting element may be a cutting blade, and preferably has a cylindrical shape.

The clamping element may be an expansion element, such as a balloon, or may be formed of rigid materials, such as a clamp pad. The clamping element may also be adapted to prevent a tissue plug from entering the vessel, the tissue plug comprising the portion of the wall removed when the hole may be formed in the vessel. In this regard, if the clamping element is a balloon, it is preferred that the balloon have a diameter smaller than that of the cutting element, and that the balloon not be deflated after being used as the clamping element.

The system further comprises a graft protection element adapted to prevent the graft from being damaged by the cutting element. In this case, the clamping element and the graft protection element may be the same element, for example, an expansion element, which may be expandable from an unexpanded state to fully expanded state and to a partially expanded state. The expansion element may be a balloon, which may be in the shape of a circular toroid, and may include a tension member that restricts the dimensions of the balloon. In addition, the expansion element may be an umbrella mechanism.

The retraction element may comprise a graft attachment tool, which is preferably radiopaque. The retraction element may be further adapted to be withdrawn from the hole formed in the wall of the vessel after entering into engagement with the graft, thereby withdrawing a portion of the graft. The portion of the graft withdrawn by the retraction element is preferably the side branch portion.

The invention also relates to a graft device adapted to be used in the formation of a side branch in a hollow vessel. The graft device comprises a graft containment element, which is adapted to contain the graft in a compressed state, a graft element including a main vessel portion and a side branch portion, the graft element being adapted to be contained with the graft containment element in a compressed state, and a graft attachment element, which is adapted to enter into engagement with a corresponding attachment element. The graft containment element may comprise a sheath, a chain stitch, or the like. As used herein, a chain stitch comprises a series of loops or slipknots that are looped through one another such that one slipknot in the stitch prevents the next slipknot from releasing. The graft attachment element may comprise a loop, and is preferably radiopaque. The graft device may also comprise a graft protection element. Furthermore, the side branch of the graft may be occluded, and the graft device may further comprise a means for opening the occlusion in the side branch portion. Moreover, the compressed state of the graft may comprise a folded configuration, a partial inside-out configuration, or the like. When the graft containment element is removed from the graft, the graft element expands from a compressed state to an expanded state. In addition, the graft device may comprise separate graft containment elements for each of the main vessel and side branch portions of the graft device, thereby allowing each portion to expand from its compressed state separately.

It should be noted that the clamping element and the graft protection element may be combined into a single element. For example, the functionality of the clamping element and the graft protection element may be obtained using a single expansion element. Such an expansion element may be expandable from an unexpanded state to fully expanded state and to a partially expanded state. Examples of expansion elements include balloons and umbrella mechanisms. If the expansion element is a balloon, it is preferred that the balloon be in the shape of a circular toroid. Optionally, a tension member may be included that restricts the dimensions of the balloon.

The present invention also provides a means for expanding the expansion element from the unexpanded state, to the fully expanded state, and to the partially expanded state in a sequential manner. In the fully expanded state, the expansion element preferably has an outer diameter larger than an outer diameter of the cutting element. In the partially expanded state, the expansion element preferably has an outer diameter that is less than an inner diameter of the hole forming element and greater than an outer diameter of the retraction element to thereby position a tissue plug within the hole forming element. Also, if the expansion element is a balloon, the means for expanding may comprise a syringe in fluid communication with the balloon. If the expansion element is an umbrella device, the means for expanding may comprise a cylinder having a piston slideable therein and coupled to the umbrella device.

Furthermore, the present invention provides a sequencing means for coordinating at least one of holding the position of the applicator relative to the vessel with the positioning element, cutting a hole in the wall of the vessel with the cutting element, inserting the an insertion element through the wall of the vessel, entering the retraction element into engagement with the graft, and withdrawing the retraction element from the hole formed in the wall of the vessel. The sequencing means may comprise a cam mechanism, a gear mechanism, at least one servo mechanism operatively coupled to the applicator and a controller operatively coupled to the at least one servo mechanism, and the like. The controller may comprise a microprocessor based device. In addition, a button may be operatively coupled to the sequencing means for activating the sequencing means upon depression of the button to thereby accomplish steps of a procedure for forming the hole in the vessel. Furthermore, the sequencing means may coordinate the expansion state of the expansion element with respect to the relative movement of the cutting element and the clamping element.

DETAILED DESCRIPTION OF THE INVENTION

Figure 1:
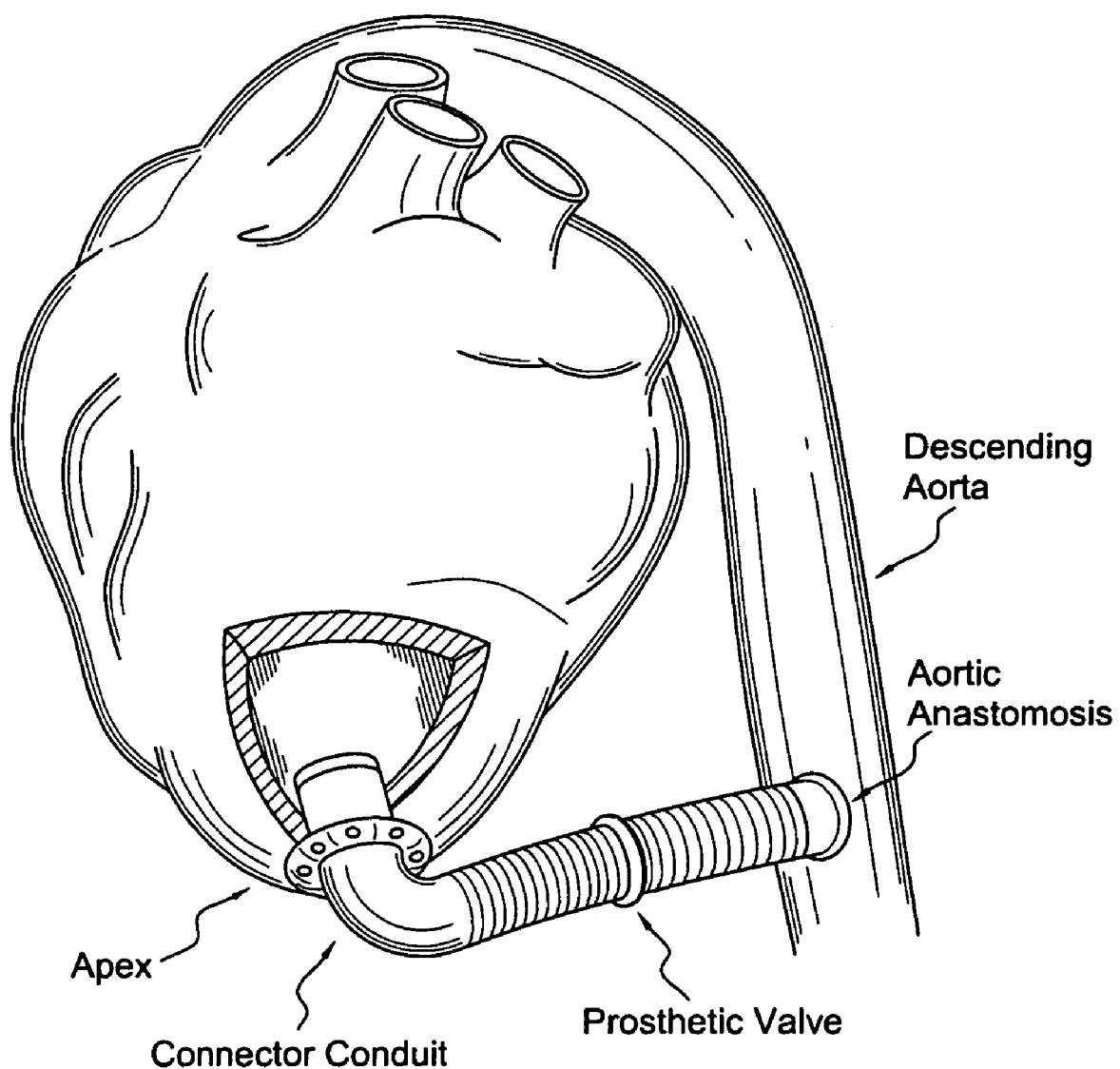
FIG. 1 is a schematic of a conventional apicoaortic conduit.

The present invention addresses the anastomosis between the apicoaortic prosthesis and the descending aorta. Primarily because of the difficulty reaching this anastomosis, this portion of the procedure remains highly invasive, time consuming and technically challenging. Also, it is well recognized that the partial occlusion clamp used in the conventional apicoaortic procedure can harm the aorta walls and can dislodge debris from the inner aortic wall.

More and more, operating rooms are incorporating fluoroscopy to allow combined efforts of surgeons and interventional radiologists during a single procedure. This trend is expected to continue. As such, the present invention combines a percutaneous (or endovascular) approach with a minimally invasive surgical approach. The goals of the present invention are to provide surgical and interventional tools and prostheses to enable the descending aorta anastomosis to be less time consuming, less technically challenging, and to be performed with minimal blood loss. Moreover, use of a partial occlusion clamp is eliminated.

The present invention makes use of advances in percutaneous repair of abdominal and thoracic aortic aneurysms. Several companies now offer vascular grafts that are percutaneously delivered and implanted at the aneurysm site. Examples of related inventions are described in U.S. Pat. Nos. 6,551,350, 6,843,803, and 6,827,735. Some inventions have presented side branches from the main vascular graft for deployment at the renal arteries or at the aortic arch, for example; however, none of these inventions have provided the necessary surgical tools and modifications to the aortic graft for a side branch to serve as the anastomosis between the apicoaortic prosthesis and the descending aorta.

The present invention also enables an alternative use of prosthetic valves that are currently under development for percutaneous aortic valve replacement, such as described in U.S. Pat. No. 6,893,460 by Spenser, et al. Although these valves are typically intended for percutaneous delivery and deployment at the native aortic valve location, these valves could be delivered percutaneously for use in the apicoaortic conduit.

Thus, the present invention provides a system comprising the complete apicoaortic prosthesis according to the preferred embodiment includes a rigid apical connector portion which will serve to provide egress from the left ventricle (such as from the apex or lateral wall), a flexible conduit portion which will carry blood from the connector to the arterial system (such as to the descending thoracic aorta), and the aortic valve itself, which will be situated somewhere within the conduit. The present invention primarily addresses attachment of a flexible conduit portion to the arterial system. The present invention includes an implantable aortic connector and the necessary instruments to position, deploy and secure the device.

In addition, the present invention allows the surgeon to precisely select a site along the descending aorta where an anastomosis between an aortic connector and descending aorta will be formed. The site selection may be based upon imaging performed prior to bringing the patient to the surgical suite, such as computer aided tomography imaging. Site selection may also include minimally invasive ultrasound imaging and visual inspection. After selecting the anastomosis site, the surgeon introduces a placement instrument or applicator through a small incision between the ribs that requires little or no rib spreading. The distal end of the applicator is then inserted through the aortic wall at the selected site. The interventional radiologist or cardiologist (the interventionalist) then delivers an unexpanded aortic connector to the selected site and attaches the aortic connector to the applicator, thereby precisely placing the aortic connector at the selected anastomosis site. The aortic connector can then be deployed by expanding an aortic graft inside the aorta. Then a side branch can be pulled from within the aortic graft to be attached to the remainder of the apicoaortic prosthesis. The side branch may include a quick connect coupler. Some occlusion means is needed to prevent blood loss until the aortic connector is attached to the remainder of the apicoaortic prosthesis and the surgeon is ready to begin blood flow. This occlusion means may be a sewn seam that is removed to allow blood flow. Alternatively, the occlusion means could be a prosthetic valve, which is an integral part of the apicoaortic conduit. The prosthetic valve serves as a check valve, eliminating the need for a separate occlusion means, such as a sewn seam.

Referring now to the figures, FIG. 1 is an illustration of an apicoaortic conduit, which extends from the apex of the left ventricle to the descending aorta with a prosthetic valve positioned within the conduit. The present invention includes an aortic connector that serves to create an effective aortic anastomosis. The preferred embodiment of the present invention includes aspects of the aortic connector and an applicator used to implant the aortic connector.

Figure 2A:
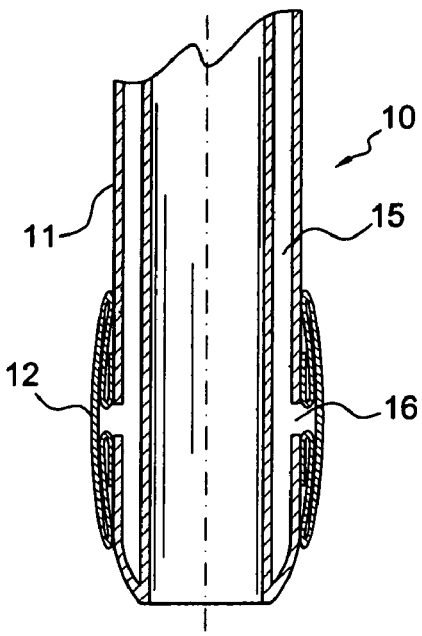
FIGS. 2A to 2E are schematics of the retractor with trocar tool and attachment tool.
Figure 2B:
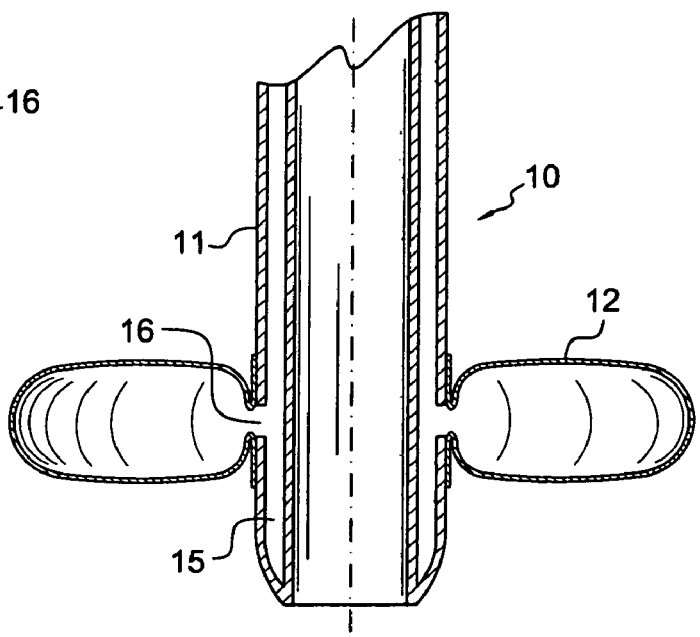
Figure 2C:
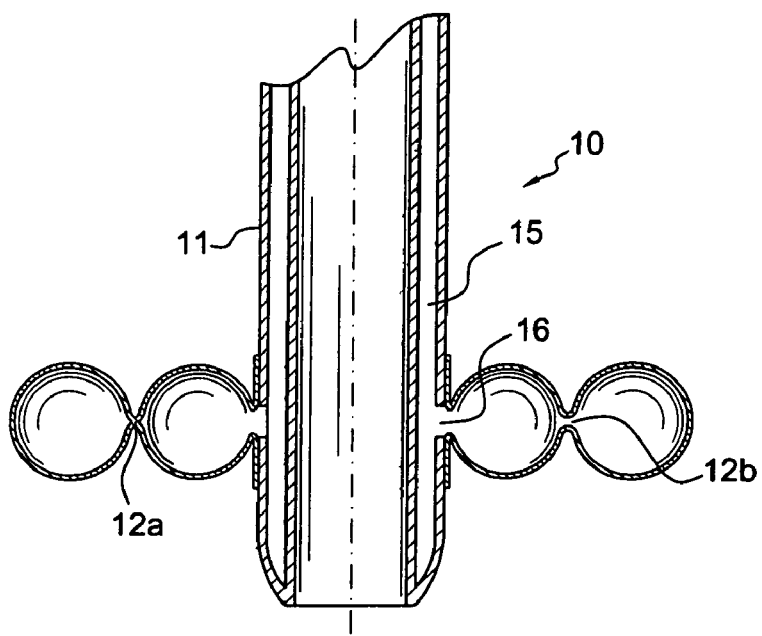

FIGS. 2A to 2E illustrate an embodiment of the distal end of a retractor 10 which will be inserted through the aorta wall. The retractor 10 includes a hollow retractor housing 11. In use, the retractor housing 11 extends from inside the descending aorta to outside the chest wall. In one embodiment, a balloon 12 is mounted onto the distal end of the retractor housing 11. The balloon 12 may be made of polyurethane, for example. A flow passage 15 extends from a syringe, for example, located outside the chest wall through an opening 16 in the retractor housing 11 and to the interior of the balloon 12. In use, the balloon 12 may be inflated with saline. Applying a pulling force to the retractor housing 11 pulls the inflated balloon snugly against the inside wall of the aorta. To reduce the volume of balloon 12 and to decrease the flow resistance resulting from the presence of balloon 12 in the aorta, balloon 12 may include joints, or tension members, 12a in the form of point or line connections, as shown in FIG. 2C. The balloon joints 12a must include small separations 12b to allow for fluid entry and exit to all portions of the balloon 12. The balloon joints 12a serve as tension members that limit expansion of balloon 12.

Figure 2D:
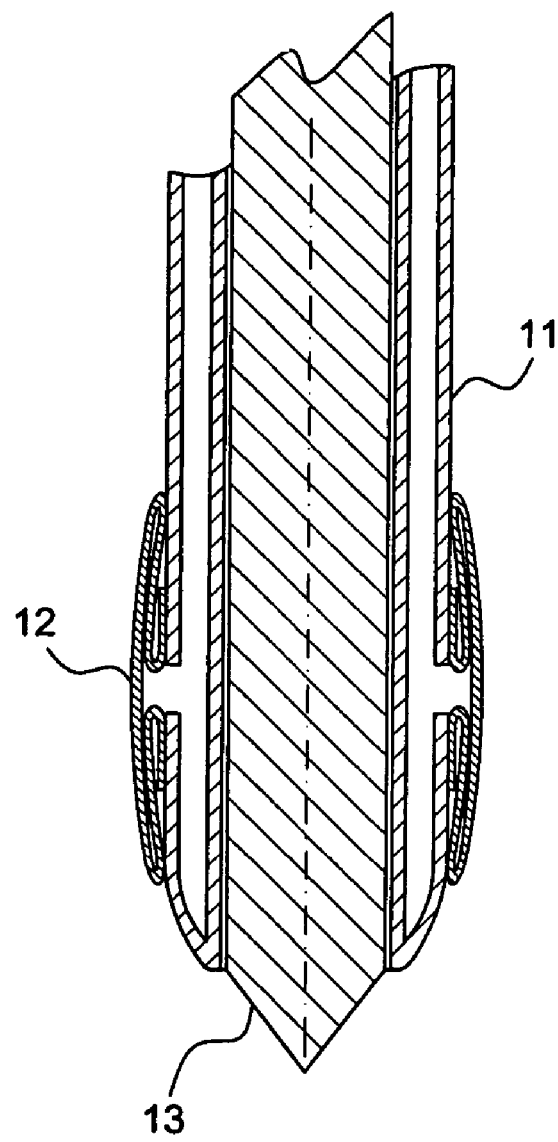
Figure 2E:
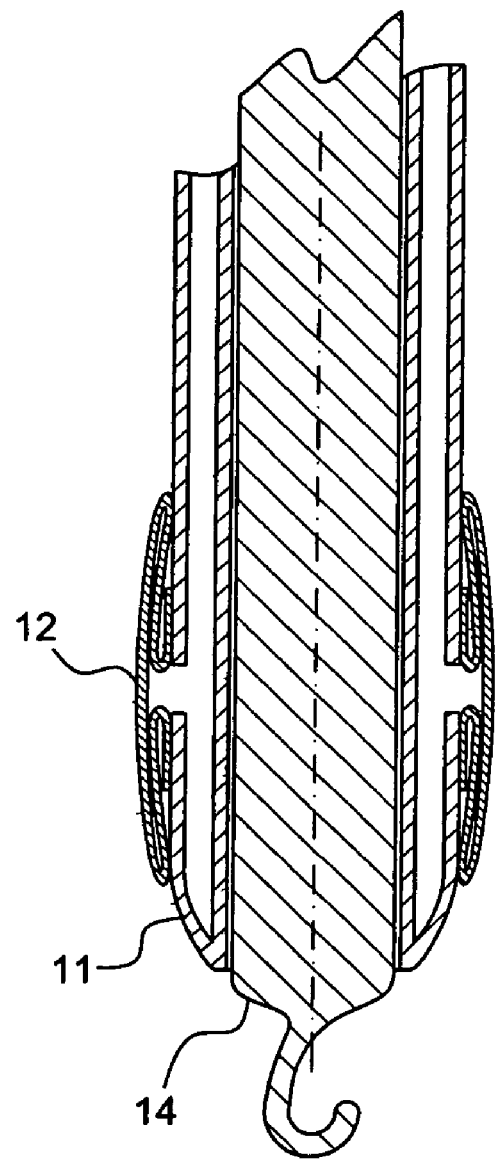

FIG. 2D illustrates a trocar tool 13 mounted inside the retractor housing 11. The trocar tool 13 may be inserted and removed from the retractor housing 11. The trocar 13 is used to make a hole in the aorta wall through which the distal end of the retractor 10 is inserted. The trocar 13 may be spring loaded with a mechanism to allow quick retraction of the trocar 13 into the retractor housing 11 after the hole is made in the aorta wall, thereby preventing accidental damage to the aorta wall. FIG. 2E illustrates a radiopaque attachment tool 14, shown as a simple hook. The attachment tool 14 may be inserted and removed from the retractor housing 11. In use, the attachment tool 14 is used to position folded aortic connector 50 precisely with respect to the applicator. Attachment tool 14 may also be a guidewire (separate from guidewire 55) inserted through retractor housing 11 and extending to a distal site, such as to a percutaneous entry site through the femoral artery at the groin. The hollow retractor housing 11 includes a check valve that prevents blood loss from the aorta when the trocar tool 13 or attachment tool 14 is not inserted. This check valve allows insertion of the trocar tool 13 and attachment tool 14 without damage to the check valve.

In addition to the retractor 10, the applicator includes a reaction tube 30 and a cutter tube 20, both located concentrically with the retractor 10, as illustrated in FIGS. 3A to 3I. Cutter tube 20 includes a sharp edge 20a. A description of how the applicator is used to implant the aortic connector 50 will be used to further describe these components.

Figure 3A:
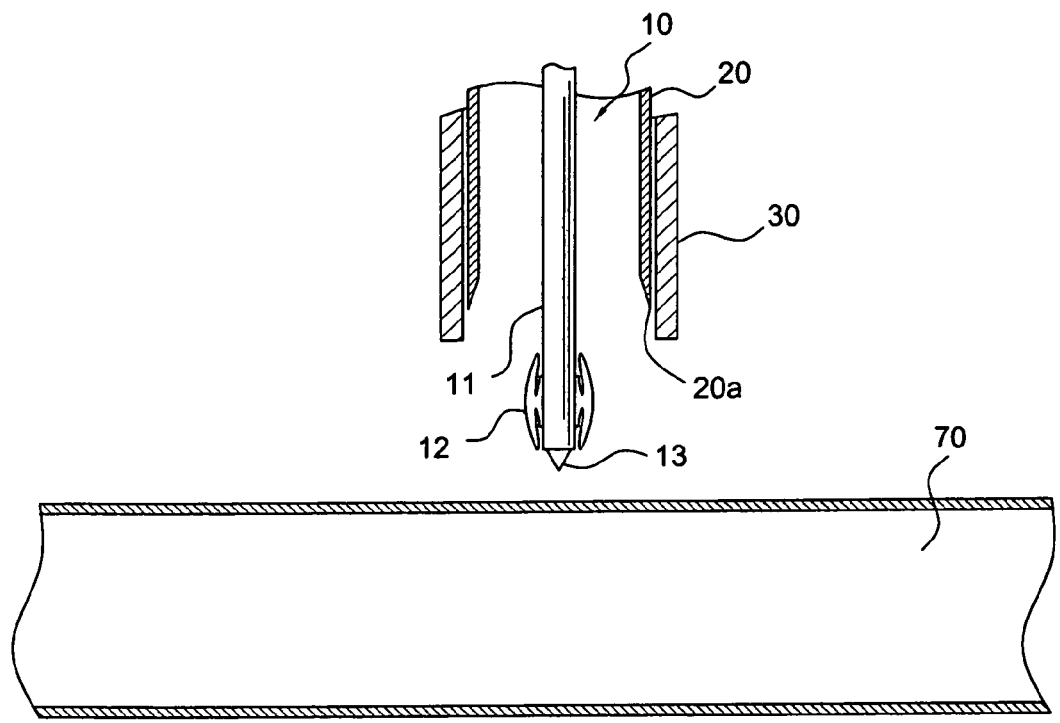
FIGS. 3A to 3I illustrate operation of an applicator to deploy the aortic connector.

The applicator shown in FIG. 3A used to position the aortic connector 50 consists of a retractor 10, a reaction tube 30, and a cutter tube 20. Movements and actions of these elements and components of these elements may be coordinated manually or by mechanisms which reside primarily outside the chest wall. These mechanisms may be controlled independently or in a coordinated manner, such as by using a cam mechanism similar to those described in U.S. patent application Ser. No. 11/086,577.

Figure 3B:
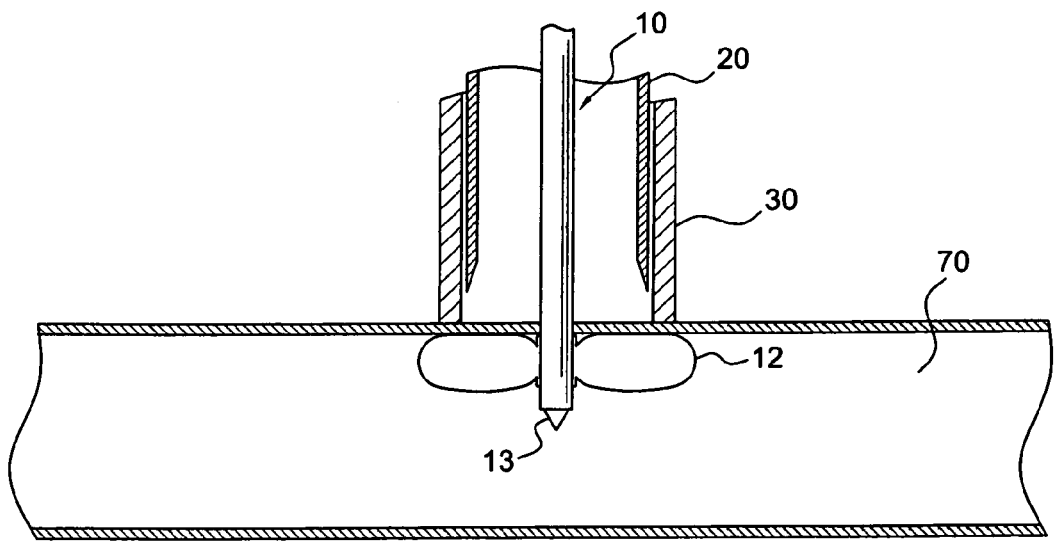
Figure 3C:
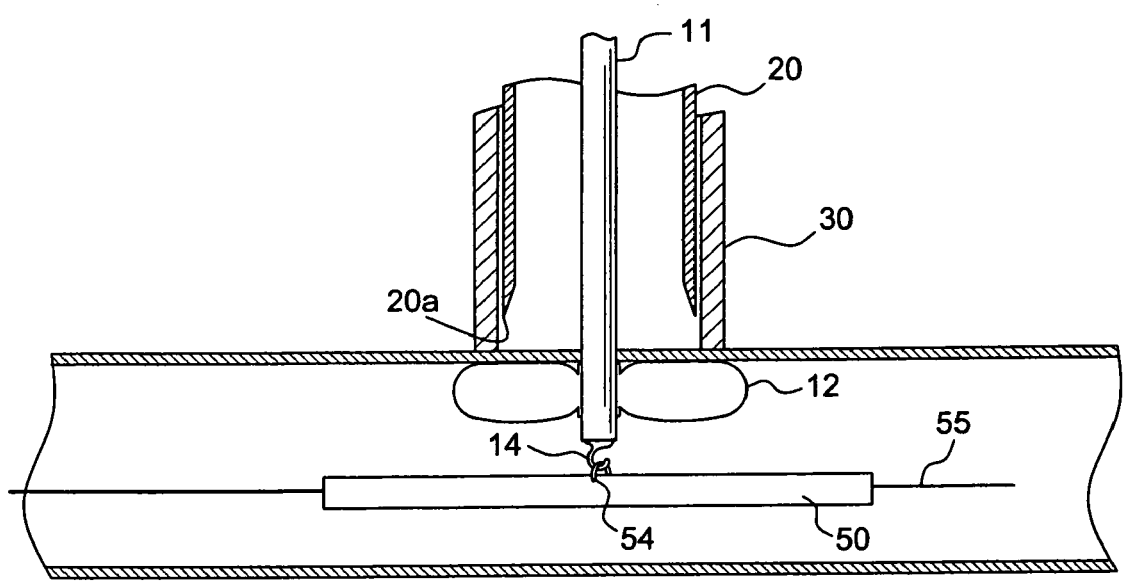
Figure 3D:
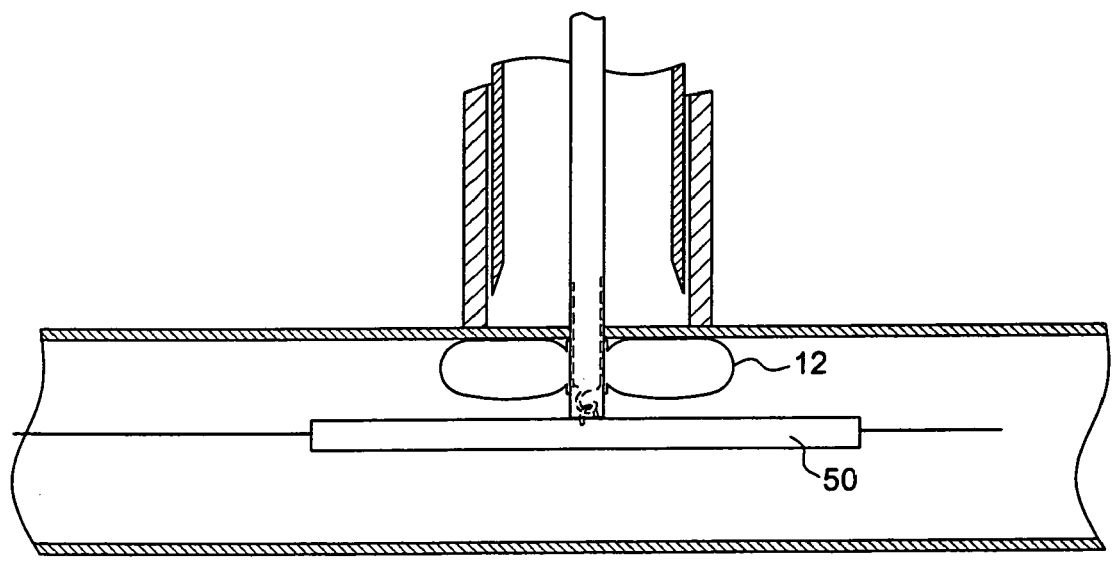
Figure 3E:
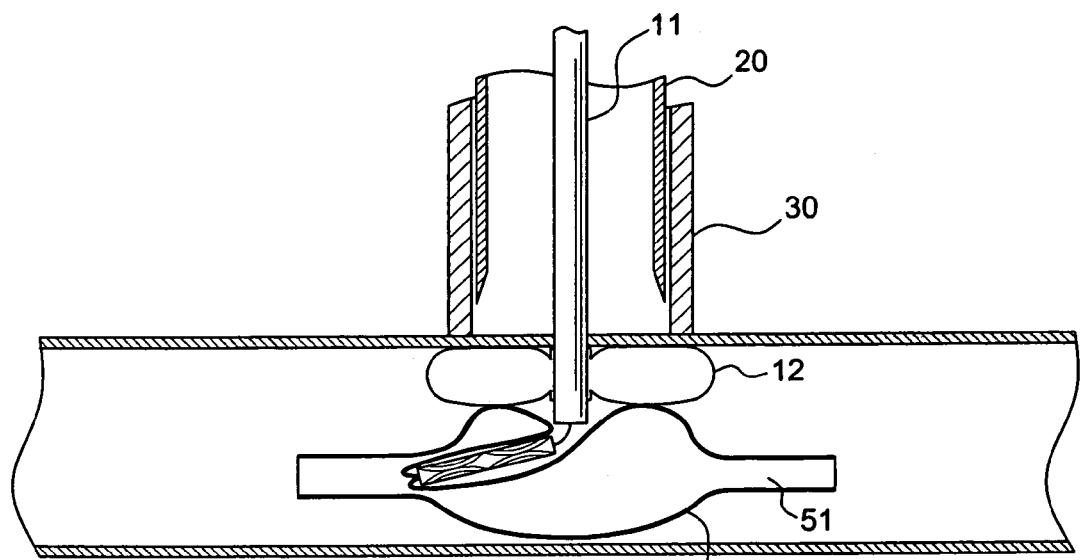
Figure 3F:
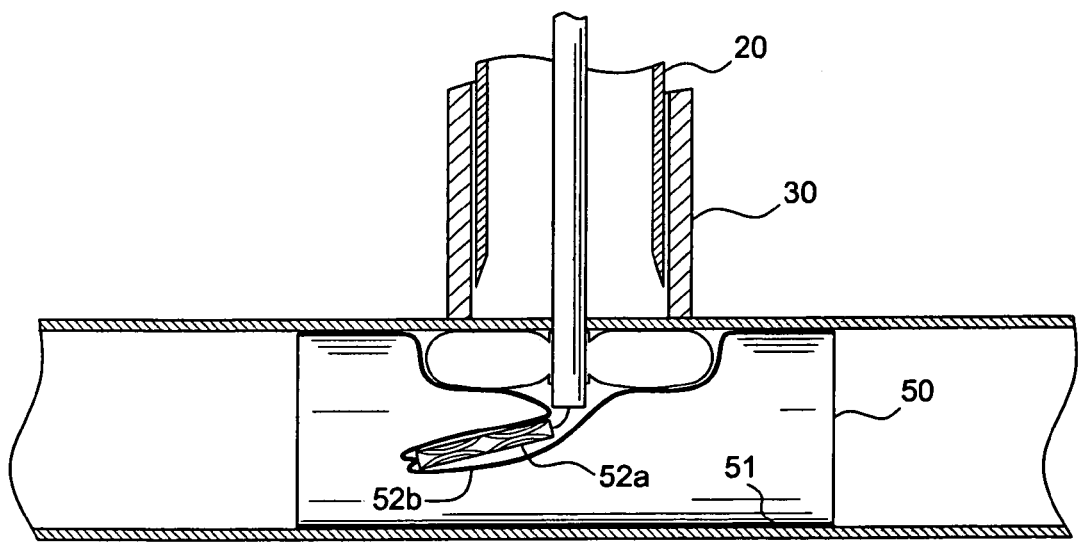
Figure 3G:
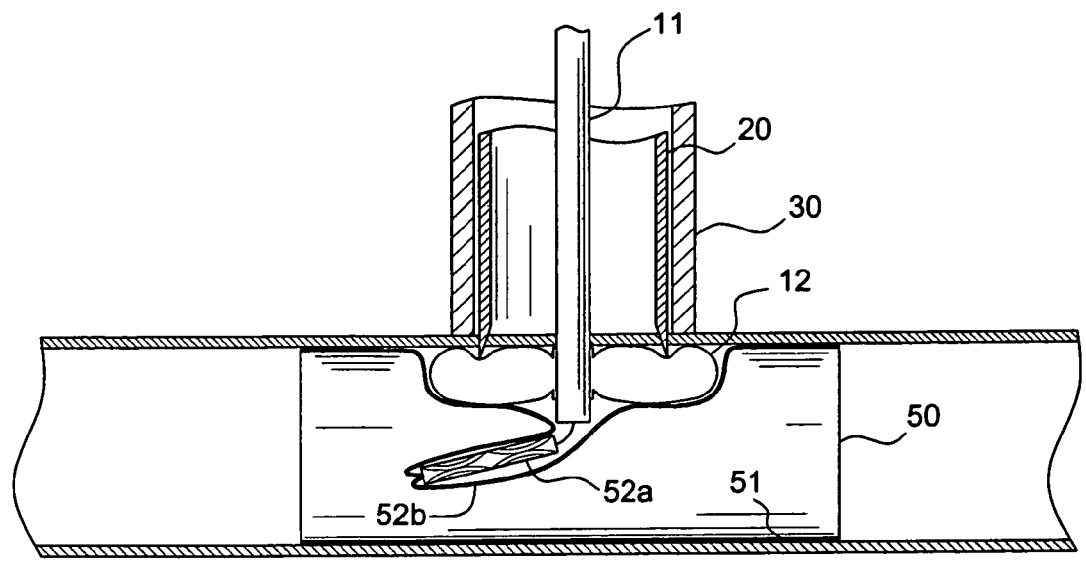
Figure 3H:
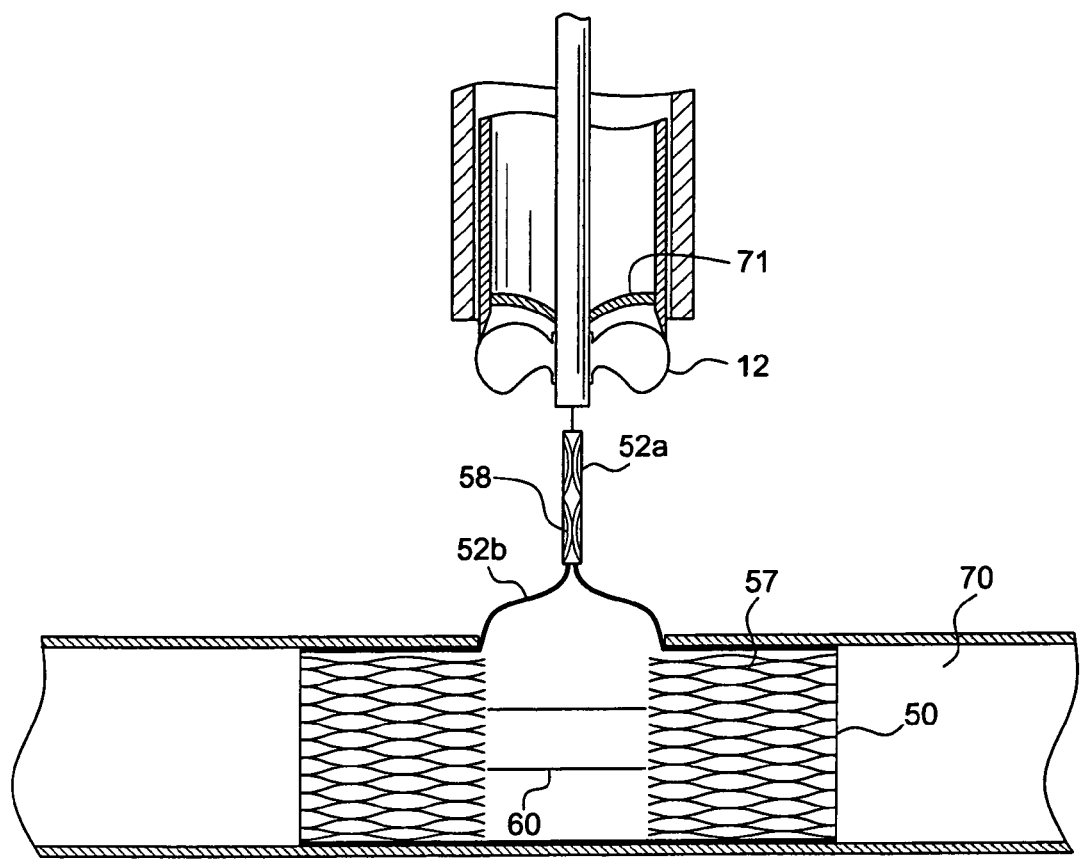
Figure 3I:
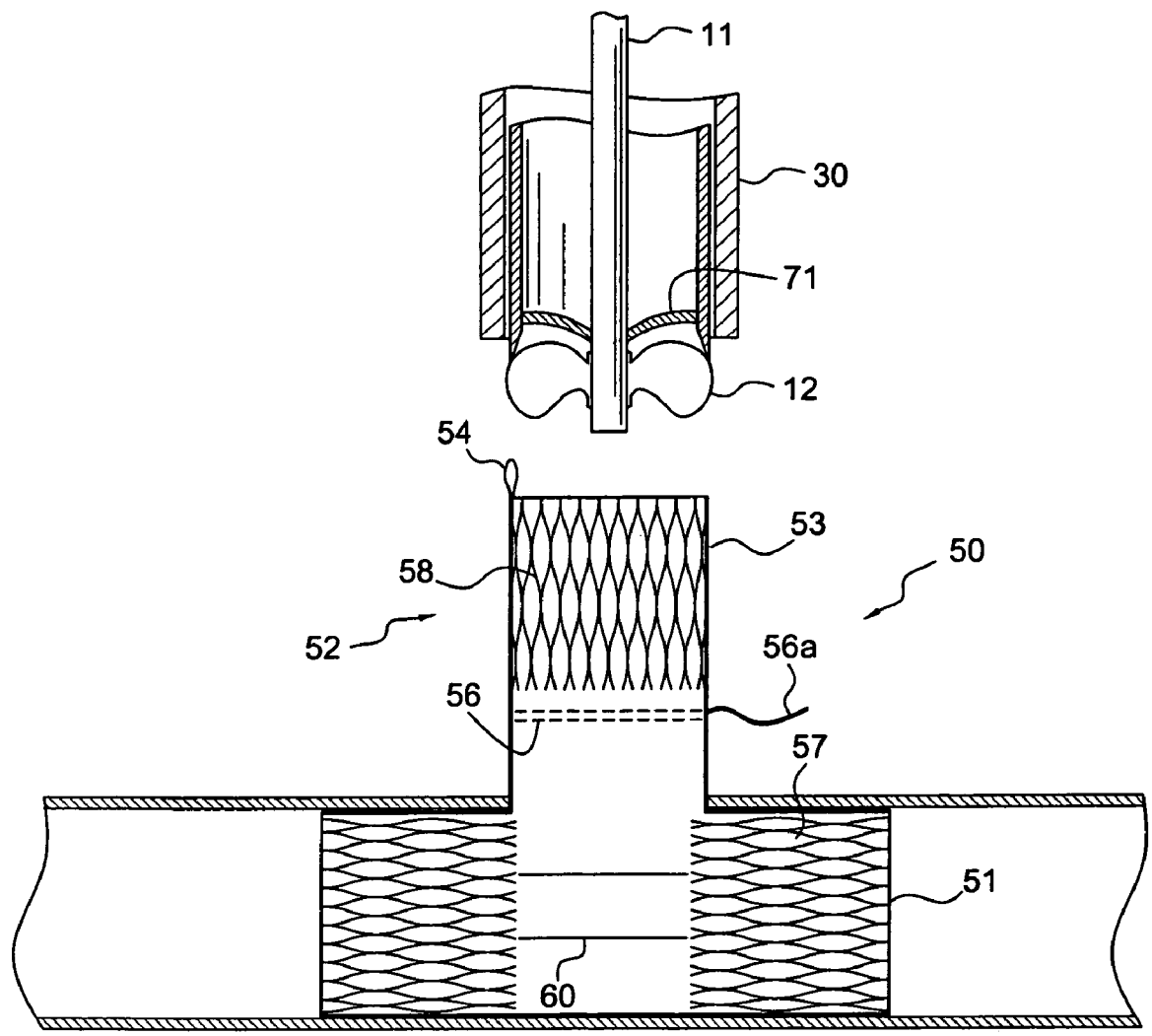

Both percutaneous and minimally invasive surgical techniques are used to implant the aortic connector 50 (FIG. 3I). A fluoroscope is required for the percutaneous aspects of the procedure. The aortic connector is percutaneously delivered from the femoral artery in the groin to its final position in the descending aorta. The aortic connector 50 may be folded to a diameter of 19 Fr (6 mm), for example, for percutaneous delivery. Visualization of the surgical aspects of the procedure may be achieved with a 10-mm diameter videoscope, for example. Three to five small incisions between the ribs are needed for the videoscope and for minimally invasive surgical tools, including the applicator described herein.

The surgical portion of the procedure includes dissection of the descending aorta from the surrounding soft tissue in the area where the side branch portion 52 (FIG. 3I) of the aortic connector 50 will pass through the aortic wall. Computerized tomography may be performed prior to the surgery to identify an acceptable region of the descending aorta for the side branch 52 to pass through the aortic wall. In the operating room, ultrasound may be used to confirm the desired location for the aortic connector 50. Such ultrasound device may be of a wand configuration to penetrate a small incision between the ribs to precisely locate any calcium islands or other diseased areas of the aorta that should be avoided. Once the precise location where the side branch portion 52 of the aortic connector will pass through the aorta wall is chosen, the surgeon is ready to use the applicator, as described next.

A first embodiment of the present invention is shown in FIGS. 3A to 3I. FIG. 3A illustrates the distal end of the applicator with retractor 10, cutter tube 20, and reaction tube 30. The applicator is shown outside the aorta 70 with balloon 12 deflated. The trocar tool 13 is inserted into the retractor housing 11. (Details of retractor housing 11 and flow passage 15 are shown in FIG. 2D.) Once the desired location where the side branch portion 52 of the aortic connector 50 will pass through the aorta is chosen, the retractor 10 with trocar tube 13 is inserted through the aorta wall and progressed until reaction tube 30 is pressed against the outer wall of the aorta, as shown in FIG. 3B. Then, balloon 12 is inflated. Then, retractor 10 is moved axially with respect to the reaction tube 30 and cutter tube 20 until the aorta 70 is firmly sandwiched between the balloon 12 and reaction tube 30. A spring may be used to move the retractor 10 relative to the reaction tube 30 and to provide the compressive force to sandwich the aorta wall. Alternatively, this compressive force may be provided by the inflation of balloon 12 so that no axial movement of retractor 10 is needed to firmly sandwich, or clamp, the aorta wall between the reaction tube and the balloon.

FIG. 3C illustrates percutaneous introduction of aortic connector 50 along guidewire 55. The aortic connector 50 is shown in a folded configuration to reduce its diameter to allow percutaneous introduction. The side branch portion 52 is stored within aortic graft portion 51 in a partial inside-out configuration shown more clearly in FIG. 3E to FIG. 3G. The folded configuration may be achieved by putting aortic connector 50 into a sheath which is removed to allow stent expansion of the aortic graft 51 to its final position. A separate sheath could allow stent expansion of quick connect coupler 53 of the side branch 52. Alternatively, the aortic connector 50 could be held in its folded configuration by a restraining member such as a chain stitch that is released by pulling a thread on one end of the stitch, as described in U.S. Pat. No. 6,551,350 by Thornton, et al. Such restraining member holds the aortic graft 51, which has an integrated stent, in a folded configuration until the restraining member is released. Whether held in a folded configuration by a sheath or other restraining member, unfolding or expansion of the aortic connector 50 propagates from the middle of the aortic graft 51 towards both ends, as described later and shown in FIG. 3D to FIG. 3F. At this middle position along the aortic graft 51 is a radiopaque attachment hook or loop 54 which the interventionalist connects to radiopaque attachment tool 14. Attachment loop 54 may be connected to the end of side branch portion 52, as shown in FIG. 3H, for example. In use, once the folded aortic connector 50 is percutaneously delivered to the vicinity of where the retractor 10 has been inserted into aorta 70, the attachment tool 14 and attachment loop 54 are manipulated by the interventionalist until they are joined, as shown in FIG. 3C. Fluoroscopy may be used to facilitate this attachment. Once the aortic connector 50 is attached to the applicator, attachment tool 14 may be partially retracted into retractor housing 11 to closely position the end of side branch portion 52 where it will pass through the aortic wall, as illustrated in FIG. 3D.

FIG. 3E and FIG. 3F illustrate deployment of the aortic graft portion 51 of aortic connector 50. Deployment of aortic graft 51 is arranged to position the side branch 52 at the precise location of where side branch 52 will pass through the aortic wall. Such deployment is achieved by allowing the stent to expand the aortic graft from the middle outwards, as shown in FIG. 3E and FIG. 3F. Such expansion may be achieved by removing sheaths from both ends of the aortic graft 51 or by a restraining member that propagates expansion from the middle of the graft outwards.

The aortic graft 51 is shown fully deployed in FIG. 3F. Also shown in FIG. 3F is the side branch portion 52 of aortic connector 50. Side branch portion 52 is shown with about half of its length in a folded configuration 52a with the rest in an unfolded configuration 52b (see FIG. 3H and FIG. 3I). In a preferred embodiment, the folded portion 52a of side branch 52 serves as the female quick connect coupler 53. The folded portion 52a may be held in this configuration by a sheath or other restraining member, similar to the means to fold the aortic graft 51. Both the folded portion 52a and the unfolded portion 52b of the side branch are shown substantially inside the aortic graft 51. Furthermore, unfolded portion 52b is shown in an inside out configuration.

FIG. 3G illustrates deployment of cutter tube 20 to remove a round tissue plug 71 (see FIG. 3H) from the aorta wall. The cutter tube 20 is moved axially with respect to the reaction tube 30 and retractor 10 by a mechanism which may reside outside the chest wall. Such mechanism may be operated independently or in a coordinated manner, such as by using a cam mechanism. Once the cutter tube 20 is deployed, the surgeon applies rotary motion to the cutter tube 20. The retractor 10 rotates with the cutter tube 20 to substantially prevent relative rotary motion between the balloon 12 and cutter tube 20. The reaction tube 30 may rotate with the cutter tube 20 and retractor 10, or, alternatively, the reaction tube 30 may not rotate. Relative rotation means must be provided to allow rotation of retractor 10 without excessive rotation of side branch 52 relative to aortic graft 51. In one embodiment, the relative rotation means is provided by preventing rotation of the attachment tool 14 relative to the side branch 52. In another embodiment, the attachment tool 14 includes a rotating joint, such as a twistable cord, between the distal hook and the main body of the attachment tool 14.

Axial motion of the retractor 10 relative to the cutter tube 20 may be controlled in a similar fashion as is described in U.S. patent application Ser. No. 11/086,577 filed Mar. 23, 2005, and in U.S. Provisional Patent Application Nos.

60/726,223 and 60/726,222, both of which were filed Oct. 14, 2005. As such, once the cutter tube 20 has removed a tissue plug 71 from the aorta 70, the balloon 12 is partially deflated, thereby assuring that the tissue plug 71 remains on the retractor 10. Also, axial motion of the retractor 10 relative to cutter tube 20 continues until the balloon is partially or totally retracted to inside the cutter tube 20. In one embodiment, the balloon 12 partially deflates automatically, after the retractor 10 reaches a predetermined axial position relative to cutter tube 20. A cam mechanism may be used to provide the automatic partial deflation. In another embodiment, the balloon 12 does not partially deflate without a deliberate action by the surgeon, such as by releasing a safety latch, which may be done by pressing a button or turning a knob.

As a safety feature, simultaneously with or after the balloon 12 is partially deflated and partially retracted inside cutter tube 20, the cutter tube 20 moves axially relative to the reaction tube 30 until the sharp edge 20*a* of cutter tube 20 is retracted to within reaction tube 30, thereby preventing the sharp edge 20*a* from accidentally cutting other tissue, as shown in FIG. 3H. Such motion may be achieved independently or in a coordinated manner, such as with a cam mechanism.

Once the balloon 12 is partially deflated and partially retracted inside the cutter tube 20, movement of the applicator relative to the aorta 70 serves to remove the side branch portion 52 from within the aortic graft portion 51 of aortic connector 50, as shown in FIG. 3H. The folded portion 52*a* of side branch 52 remains folded until released, such as by removing a sheath or by releasing a restraining member. Release of the restraining member may occur simultaneously with releasing of attachment tool 14 from attachment loop 54. Also shown in FIG. 3H is aortic graft stent 57, which was not shown in prior figures for clarity. Details of the stent 57 are well known to those in the art.

The aortic connector 50 shown in FIG. 3I consists of an aortic graft portion 51 with a side branch portion 52. The aortic graft portion 51 includes a stent component 57 to provide expansion of the graft once deployed to its final position in the aorta. The aortic graft portion 51 resides inside the aorta. The side branch portion 52 extends from the aortic graft portion 51 through the aorta wall and connects to the remainder of the prosthesis illustrated in FIG. 1. The side branch portion 52 may include an occluding means 56 to prevent blood flow through the side branch 52 until the occluding means 56 is removed. The side branch portion 52 may also include the female or male half of a quick connect coupler 53, as described in U.S. patent application Ser. No. 11/086,577. Such quick connect coupler 53 may include a stent component 58 that is compressed to a small diameter for percutaneous delivery and expands to its final diameter for use as the female or male portion of the quick connect coupler 53. The side branch portion 52 may also include a folded valve (not shown) that may serve as the prosthetic valve shown in FIG. 1. The prosthetic valve serves as a check valve in the side branch portion 52, thereby eliminating the need for a separate occluding means 56, such as a sewn seam.

The deployed aortic connector is illustrated in FIG. 3I. Side branch stent 58 has been released, either by removing a sheath or by releasing a restraining member. This stented portion of side branch 52 may serve as the female quick connect coupler 53 for attaching to the remainder of the prosthesis, as shown in FIG. 1. Occlusion means 56 can be a sewn joint that prevents blood flow through the side branch 52 until the aortic connector 50 is connected to the remainder of the prosthesis, as shown in FIG. 1, air is removed from the flow channel, and the surgeon is ready to begin blood flow through the prosthesis. In one embodiment, pulling cord 56*a* from the graft removes the occluding means. In another embodiment, the occluding means could be a valve that serves as the prosthetic valve in FIG. 1.

A second embodiment of the present invention is shown in FIGS. 4A to 4H. This embodiment replaces the balloon 12 with a solid clamp pad 17, which is rigidly attached to the distal end of retractor housing 11'. In the alternative, clamp pad 17 itself may be an expansion element, such as a balloon, which a smaller diameter than the cutting element, thereby only allowing it to function as a clamping element. Clamp pad 17 may also include spikes or hooks that penetrate the aortic wall to help prevent movement of the aortic wall relative to the clamp pad 17 after the aortic wall is firmly sandwiched between the clamp pad 17 and reaction tube 30'. Also, the reaction tube 30' in this embodiment is located concentrically between the cutter tube 20' and retractor 10'. A description of how the applicator is used to implant the aortic connector 50 will be used to further describe the components of this embodiment.

Figure 4A:
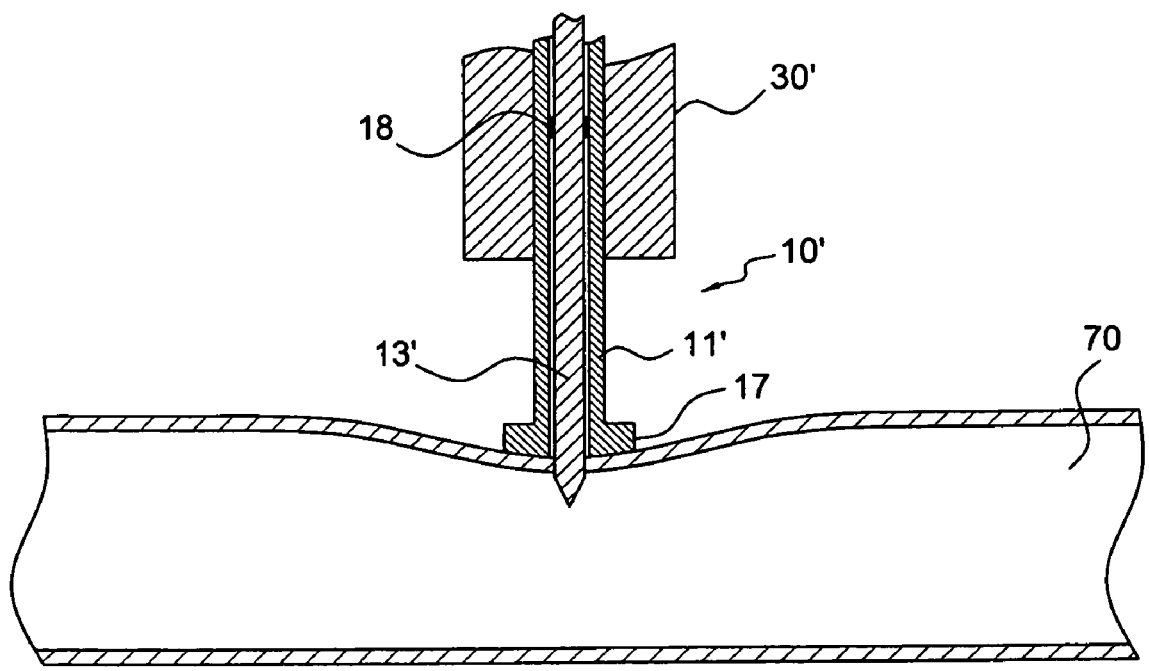
FIGS. 4A to 4H illustrate operation of an alternative embodiment of an applicator to deploy the aortic connector
Figure 4B:
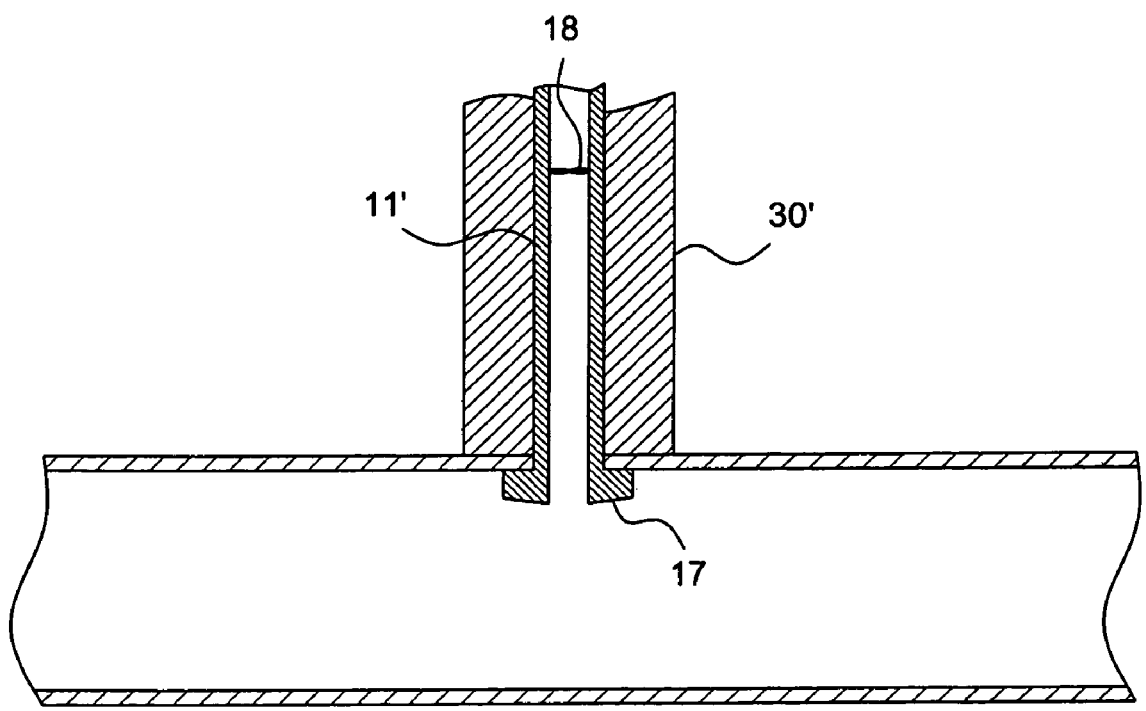

FIG. 4A illustrates the applicator with trocar tool 13' penetrating aorta 70. The trocar 13' is shaped to cut a small slit in the aortic wall of sufficient length to provide a tight or interference fit between the clamp pad 17 and the slit, with the slit being just large enough to allow clamp pad 17 to penetrate the slit. Once the slit is formed, the surgeon manipulates the clamp pad 17 to force the clamp pad 17 through the aorta wall. Manipulation of the clamp pad 17 is achieved by moving the proximal end of the retractor housing 11', which is located outside the chest wall. Once the clamp pad 17 enters the aorta 70, retractor 10' is moved axially relative to reaction tube 30' to sandwich the aorta between clamp pad 17 and reaction tube 30', as shown in FIG. 4B. A spring may be used to move the retractor 10' relative to reaction tube 30' and to provide the compressive force to sandwich the aorta wall. Alternatively, a squeeze mechanism with a mechanical ratchet may be used to clamp the aortic wall between the clamp pad 17 and reaction tube 30'. FIG. 4B also shows the trocar tool 13' removed from the retractor 10'. Check valve 18 prevents blood loss through the retractor housing 11'.

Figure 4C:
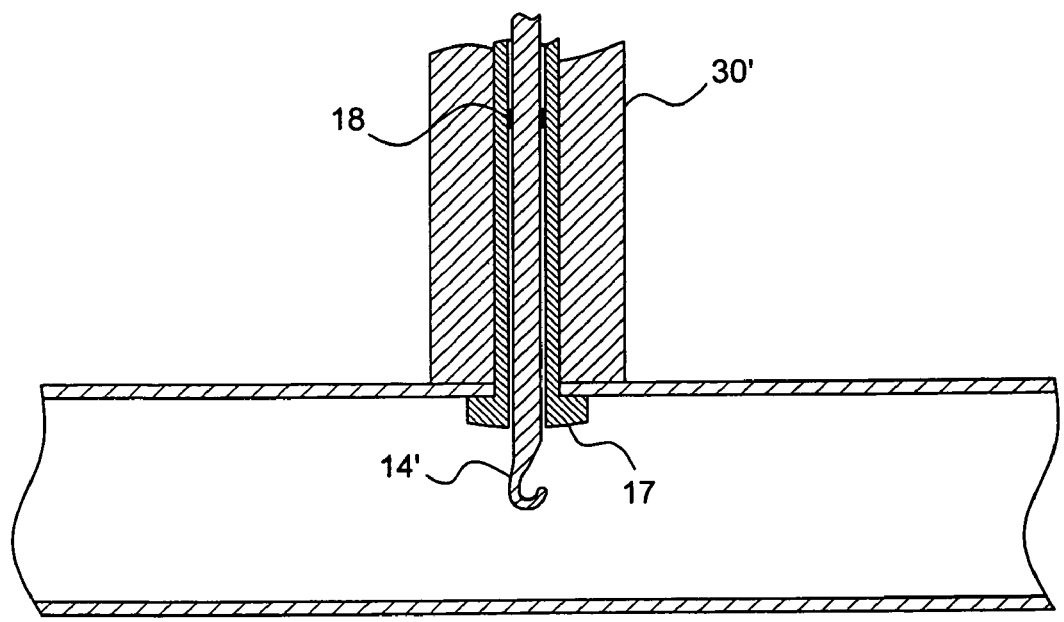

FIG. 4C illustrates introduction of attachment tool 14' into retractor 10'. The applicator with attachment tool 14' is now ready for attachment to aortic connector 50. Note that attachment tool 14' could be a guidewire (separate from guidewire 55) that is introduced from outside the chest wall through the retractor housing 11' and to a distal location, such as the percutaneous introduction site for the aortic connector 50.

Figure 4D:
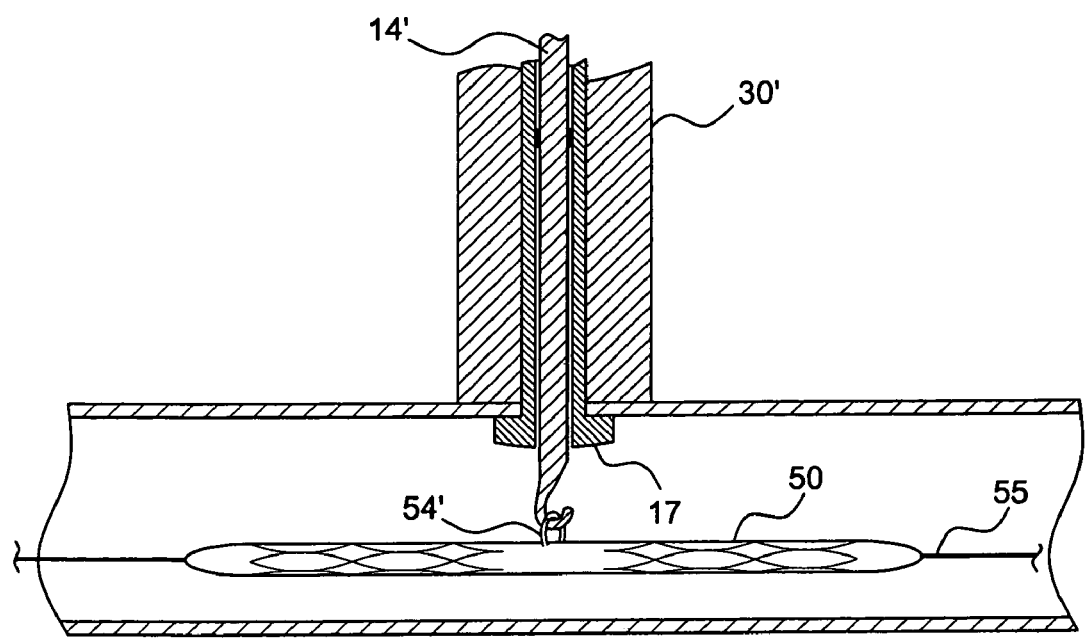

FIG. 4D illustrates percutaneous introduction of aortic connector 50 along guidewire 55. Deployment of the aortic connector 50 and details of the aortic connector 50 itself may be assumed to be the same as that described in FIGS. 3C to 3I, except for differences specifically described herein. One addition to the aortic connector 50 is a cutter guard 19 which protects the aortic connector fabric from the sharp cutter tube 20' when the tissue plug is cut, as described more fully with FIG. 4F.

Figure 4E:
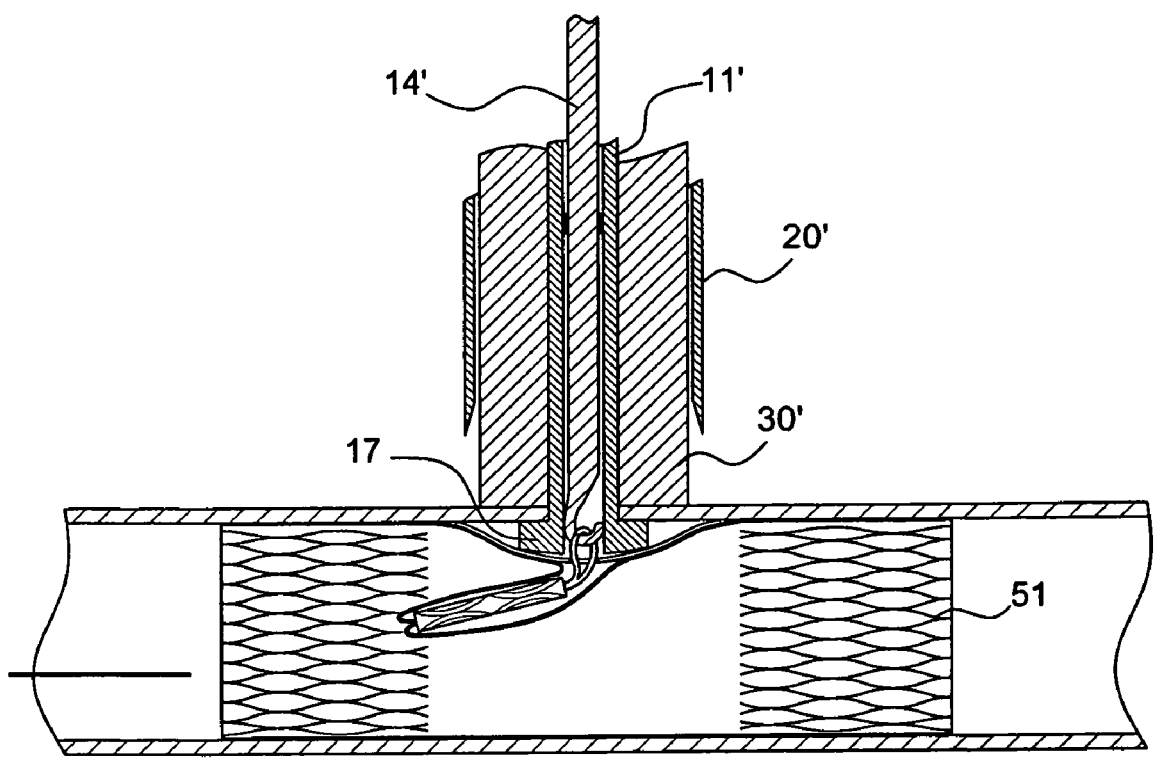

The state depicted in FIG. 4D is comparable to that of FIG. 3C. Once the aortic connector 50 is attached to the applicator, attachment tool 14' may be partially retracted into retractor housing 11' to closely position the end of side branch portion 52 where it will pass through the aortic wall. The aortic graft portion 51 of aortic connector 50 may then be expanded, as shown in FIG. 4E. Similar to FIG. 3E and FIG. 3F, deployment of aortic graft 51 is achieved by expanding the aortic graft 51 from the middle outwards. FIG. 4E also illustrates cutter tube 20'.

Figure 4F:
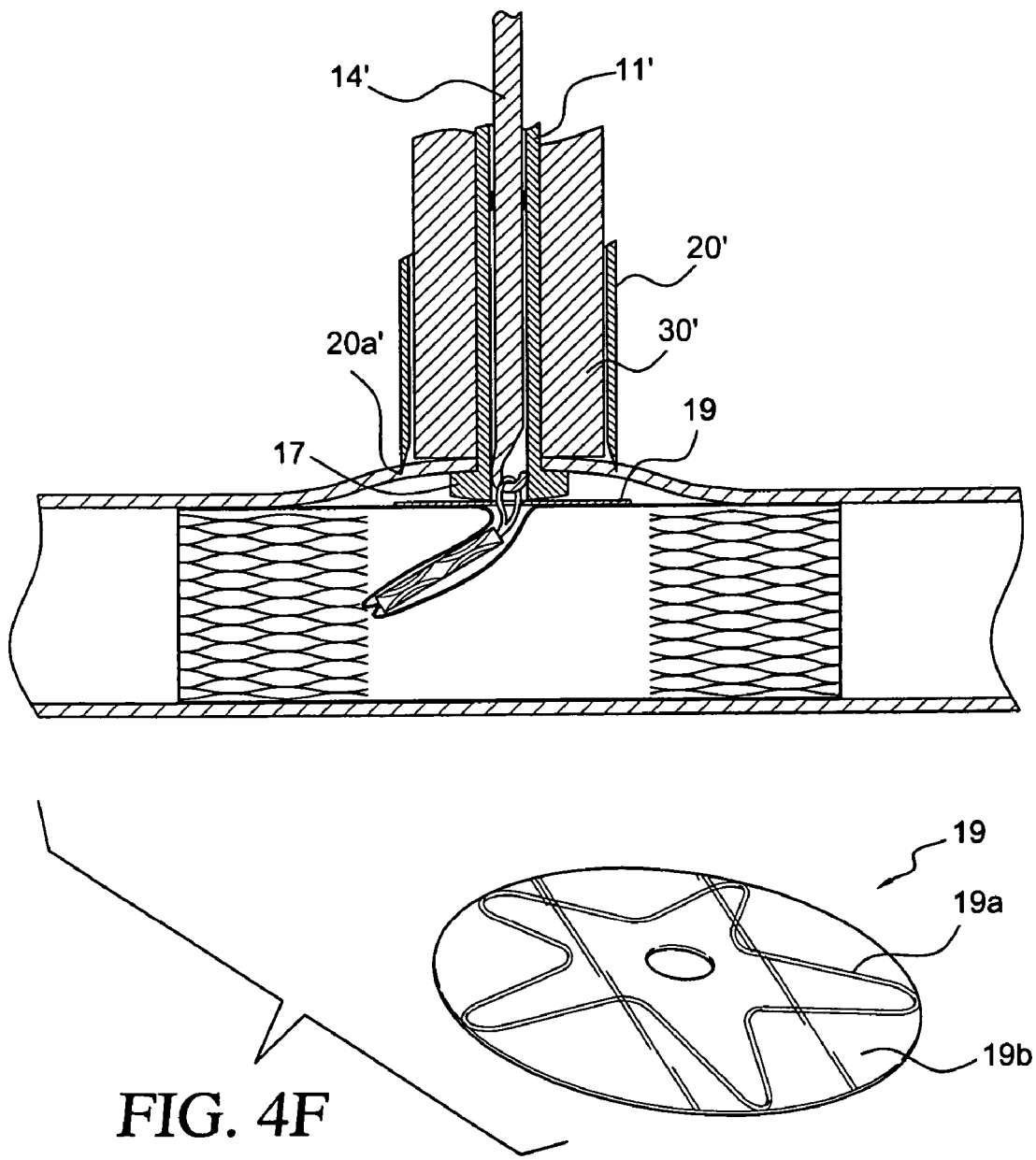

FIG. 4F illustrates deployment of the cutter tube 20' with sharp edge 20a shown partially penetrating the aortic wall. The cutter tube 20' is moved axially with respect to reaction tube 30' by a mechanism which may reside outside the chest wall. Such mechanism may use a spring to apply the axial force needed for the cutter tube 20' to cut the aortic wall. Such mechanism may be operated independently or in a coordinated manner, such as by using a cam mechanism. Once the cutter tube 20' is deployed, the surgeon applies rotary motion, if necessary, to the cutter tube 20' to create tissue plug 71. As depicted in FIG. 4F, the surgeon may also apply a slight pulling force to the applicator, thereby slightly distorting the aorta. In this way, the surgeon will readily recognize when the tissue plug 71 has been fully cut from the aortic wall.

Also shown in FIG. 4F is cutter guard 19, which resides external to aortic graft portion 51 and is rigidly connected to attachment loop 54'. (Cutter guard 19 was not shown in prior figures for clarity.) Cutter guard 19 replaces balloon 12 to protect the aortic connector 50 from the sharp cutter tool 20'. FIG. 4F shows one embodiment of a cutter guard 19, which may include a wire (e.g., nitinol) frame 19a embedded within polyurethane sheet 19b, for example. When aortic graft portion 51 is expanded, such as by removing a sheath or by releasing a restraining member, cutter guard 19 is simultaneously released. The diameter of cutter guard 19 is slightly larger than the cutter tube 20' diameter, so that the cutter guard 19 protects aortic connector 50 from sharp edge 20a.

Figure 4G:
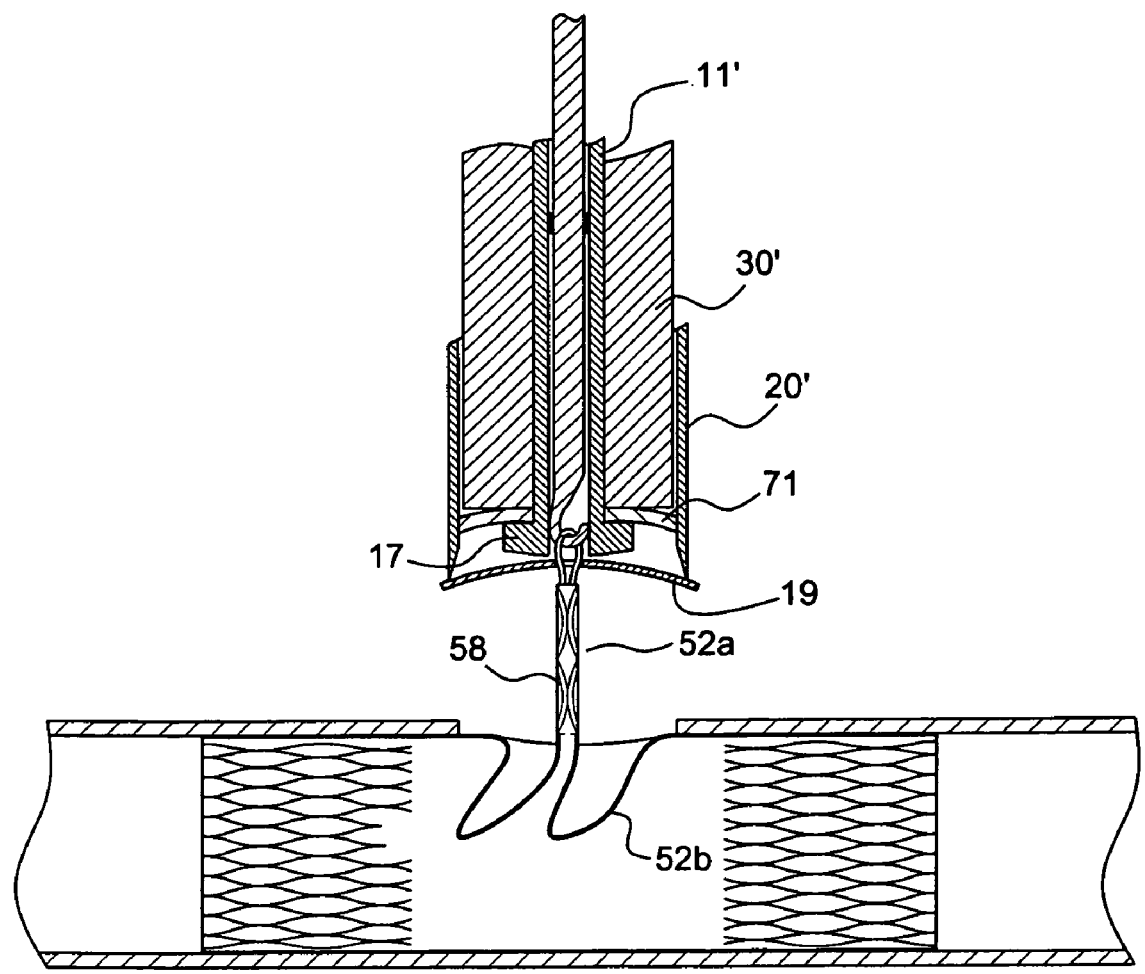

Once the tissue plug 71 is retracted to inside cutter tube 20', movement of the applicator relative to the aorta 70 serves to remove the side branch portion 52 from within the aortic graft portion 51, as shown in FIG. 4G. Cutter guard 19 is pulled against the sharp edge 20a of cutter tube 20'.

Figure 4H:
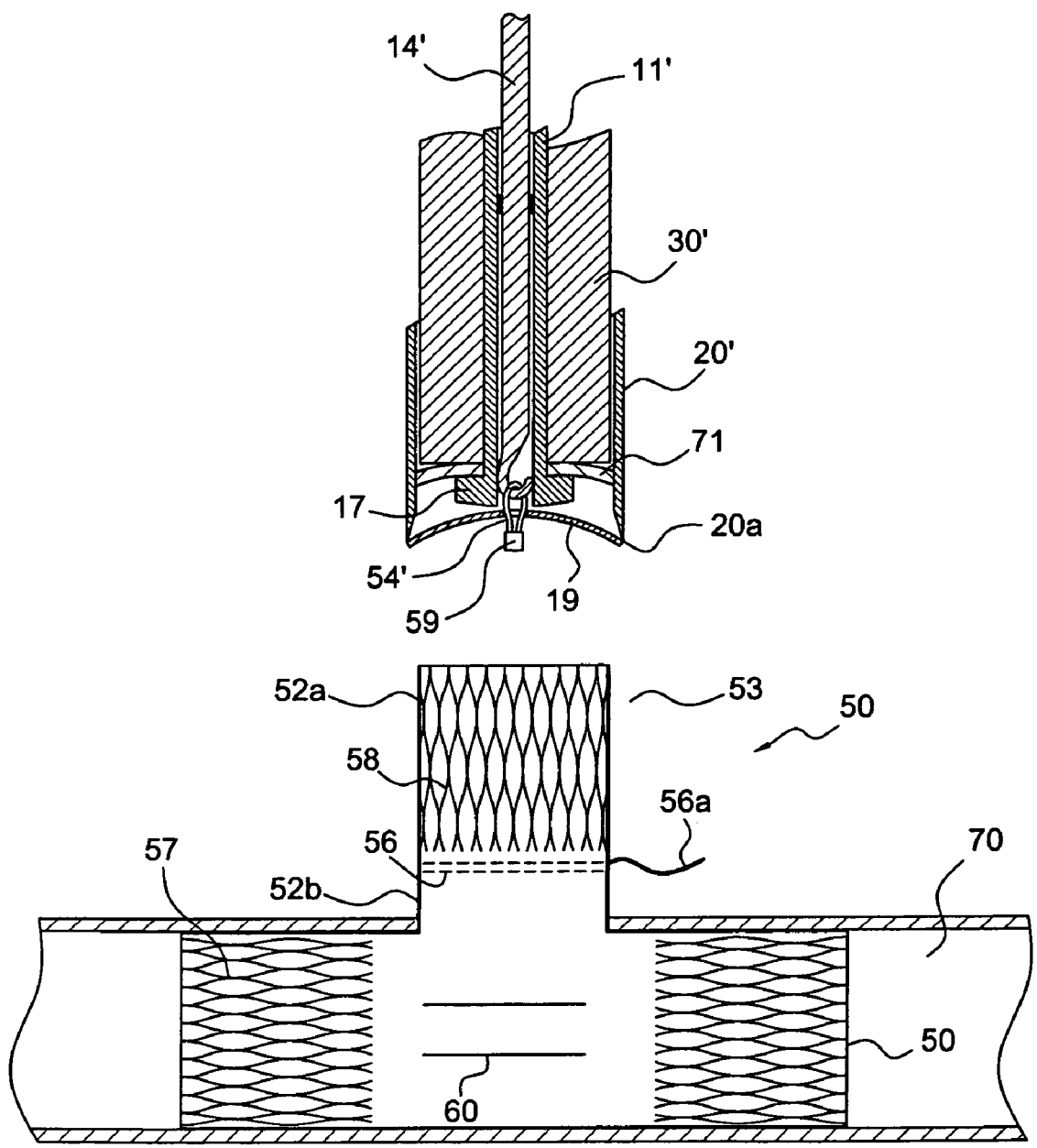

The deployed aortic connector 50 is illustrated in FIG. 4H. Side branch stent 58 has been released, either by removing a sheath or by releasing a restraining member. As an example, releasing a restraining member to expand side branch stent 58 could provide for separation from disconnect means 59, so that attachment loop 54' with cutter guard 19 and disconnect means 59 remains attached to attachment tool 14'. Prior to releasing the restraining member, disconnect means 59 is held securely within side branch stent 58. Also shown in FIG. 4H are axial stiffeners 60, which serve to maintain separation between aortic graft stents on each end of aortic graft portion 51. Axial stiffeners 60 are also shown in FIGS. 3H and 3I.

While the invention has been described with particular reference to the preferred embodiments, it will be understood by those skilled in the art that various changes may be made and equivalents substituted for elements of the preferred embodiment without departing from the invention. In addition, many modifications may be made to adapt a particular situation and material to a teaching of the present invention without departing from the essential teachings of the present invention.

As is evident from the foregoing discussion, certain aspects of the invention are not limited to the particular details of the examples illustrated, and it is therefore contemplated that other modifications and applications will occur to those skilled in the art. It is accordingly intended that the claims shall cover all modifications and applications as do not depart from the spirit and scope of the invention.

What is claimed is:

1. A method for providing a tubular side branch on a hollow vessel, the method comprising:
   providing a graft comprising (i) a tubular structure comprising a first end, a second end and a side wall extending therebetween, and (ii) a tubular side branch comprising a first end, a second end and a substantially fluid-impervious side wall extending therebetween, the first end of the tubular side branch being connected to the side wall of the tubular structure so that the interior of the tubular side branch is in fluid communication with the interior of the tubular structure, the second end of the tubular side branch comprising a grasp for engaging the second end of the tubular side branch, wherein the tubular side branch is disposed within the interior of the tubular structure, with the grasp of the tubular side branch extending out of the side wall of the tubular structure;
   providing an applicator comprising (i) an insertion element configured to be inserted through the side wall of a hollow vessel, the insertion element comprising a grasper for selectively engaging the grasp of the tubular side branch, and a retraction element for selectively applying a retraction force to the side wall of the hollow vessel from within the interior of the hollow vessel, and (ii) a cutting element in telescoping relation to the insertion element for selectively cutting through the side wall of a hollow vessel when the side wall of the hollow vessel is disposed between the retraction element and the cutting element;
   advancing the insertion element through the side wall of the hollow vessel so that the grasper and the retraction element are positioned within the hollow vessel, and advancing the graft within the interior of the hollow vessel so that the grasp of the graft is in the vicinity of the grasper of the insertion element;
   engaging the grasp of the graft with the grasper of the insertion element;
   advancing the cutting element against the outer surface of the side wall of the hollow vessel while the retraction element applies a retraction force against the inner surface of the side wall of the hollow vessel so as to form a hole in the side wall of the hollow vessel; and
   retracting the insertion element and the cutting element so as to draw the tubular side branch of the graft through the hole formed in the side wall of the hollow vessel.

2. The method of claim 1, wherein the cutting element is a cylindrical cutting blade.

3. The method of claim 2, wherein forming a hole in the side wall of the hollow vessel comprises pressing the cylindrical cutting blade into the side wall of the hollow vessel and applying torsional force to the cutting blade.

4. The method of claim 1 wherein the applicator further comprises a reaction element disposed in telescoping relation to the retraction element, and wherein the method further comprises positioning the side wall of the hollow vessel relative to the applicator, wherein the positioning step comprises:
   biasing the reaction element on the outer surface of the side wall of the hollow vessel;
   biasing the retraction element on the inner surface of the side wall of the hollow vessel; and
   holding the side wall of the hollow vessel between the reaction element and the retraction element.

5. The method of claim 1, wherein the retraction element is a balloon.

6. The method of claim 1, wherein the retraction element is made of a rigid material.

7. The method of claim 1, wherein the retraction element is adapted to prevent a tissue plug from entering the hollow vessel, the tissue plug comprising a portion of the side wall removed when the hole is formed in the hollow vessel.

8. The method of claim 1, further comprising positioning a graft protection element between the graft and the cutting element prior to forming a hole in the side wall of the hollow vessel.

9. The method of claim 8, wherein the retraction element comprises the graft protection element.

10. The method of claim 1, wherein the grasper comprises a hook.

11. The method of claim 1, wherein the grasper is radiopaque.

12. The method of claim 1, wherein the retraction element is positioned between the graft and the cutting element so as to protect the graft during the forming of the hole in the side wall of the hollow vessel.

13. The method of claim 12, wherein the retraction element is an expansion element.

14. The method of claim 13, wherein the expansion element is expandable from an unexpanded state to fully expanded state and to a partially expanded state.

15. The method of claim 14, further comprising expanding the expansion element from the unexpanded state to the fully expanded state to the partially expanded state in a sequential manner.

16. The method of claim 15, wherein the expansion element is a balloon and the step of expanding is carried out with a syringe in fluid communication with the balloon.

17. The method of claim 15, wherein the expansion element is an umbrella device and the step of expanding is carried out with a cylinder having a piston slideable therein and coupled to the umbrella device.

18. The method of claim 15, further comprising a sequencing means for carrying out the expansion of the expansion element from the unexpanded state to the fully expanded state to the partially expanded state in a sequential manner.

19. The method of claim 14, wherein, in the fully expanded state, the expansion element has an outer diameter larger than an outer diameter of the cutting element.

20. The method of claim 14, wherein, in the partially expanded state, the expansion element has an outer diameter that is less than an inner diameter of the cutting element and greater than an outer diameter of the retraction element to thereby position a tissue plug within the cutting element.

21. The method of claim 13, wherein the expansion element is a balloon.

22. The method of claim 21, wherein the balloon is in the shape of a circular toroid.

23. The method of claim 21, wherein one or more tension members restrict the dimensions of the balloon.

24. The method of claim 13, wherein the expansion element is an umbrella mechanism.

25. The method of claim 1, wherein the hollow vessel is the aorta.

26. The method of claim 1, wherein the insertion element further comprises a trocar for facilitating the step of advancing the insertion element through the side wall of the hollow vessel.

27. The method of claim 1, further comprising a sequencing means for carrying out the method.

28. The method of claim 27, wherein the sequencing means comprises a cam mechanism.

29. The method of claim 27, wherein the sequencing means comprises a gear mechanism.

30. The method of claim 27, wherein the sequencing means comprises at least one servo mechanism and a controller operatively coupled to the at least one servo mechanism.

31. The method of claim 30, wherein the controller comprises a microprocessor based device.

32. The method of claim 27, further comprising depressing a button operatively coupled to the sequencing means to activate the sequencing means.

33. The method of claim 27, wherein the sequencing means comprises means for causing the elements to assume the following states in seriatim;
 a) a first state where the insertion element is positioned within the hollow vessel;
 b) a second state where the graft is positioned within the interior of the hollow vessel;
 c) a third state in which the hole has been formed with the cutting element; and
 d) a fourth state in which the tubular side branch of the graft is withdrawn through the hole in the hollow vessel.

* * * * *